United States Patent
Nishimiya et al.

(10) Patent No.: US 10,550,154 B2
(45) Date of Patent: Feb. 4, 2020

(54) PEPTIDE LIBRARY AND USE THEREOF

(71) Applicant: Daiichi Sankyo Company, Limited, Chuo-ku, Tokyo (JP)

(72) Inventors: Daisuke Nishimiya, Sumida-ku (JP); Ryuji Hashimoto, Yachiyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 417 days.

(21) Appl. No.: 14/420,317

(22) PCT Filed: Aug. 7, 2013

(86) PCT No.: PCT/JP2013/071345
§ 371 (c)(1),
(2) Date: Feb. 6, 2015

(87) PCT Pub. No.: WO2014/024914
PCT Pub. Date: Feb. 13, 2014

(65) Prior Publication Data
US 2015/0197546 A1 Jul. 16, 2015

(30) Foreign Application Priority Data
Aug. 8, 2012 (JP) ................. 2012-176208

(51) Int. Cl.
C07K 7/08 (2006.01)
C12N 15/10 (2006.01)
C40B 50/00 (2006.01)
C07K 14/81 (2006.01)
C12Q 1/37 (2006.01)

(52) U.S. Cl.
CPC ............ *C07K 7/08* (2013.01); *C12N 15/1037* (2013.01); *C07K 14/81* (2013.01); *C07K 14/811* (2013.01); *C12N 15/1044* (2013.01); *C12N 2510/00* (2013.01); *C12Q 1/37* (2013.01); *C40B 50/00* (2013.01); *G01N 2500/00* (2013.01)

(58) Field of Classification Search
CPC .......... C07K 14/81; C07K 1/047; C07K 7/08; C12N 15/1044; C12N 2510/00; C12N 15/1037; G01N 2500/04; G01N 2500/00; C12Q 1/37; C40B 50/00
See application file for complete search history.

(56) References Cited

U.S. PATENT DOCUMENTS

| 6,423,498 | B1 * | 7/2002 | Markland | .......... | C07K 14/8114 424/9.2 |
| 7,893,007 | B2 | 2/2011 | Ladner | | |
| 2006/0234916 | A1 | 10/2006 | Miyazaki | | |
| 2008/0020394 | A1 | 1/2008 | Nixon et al. | | |
| 2011/0130338 | A1 | 6/2011 | Deperthes | | |

FOREIGN PATENT DOCUMENTS

| JP | 2008-260770 A | 10/2008 |
| JP | 2008-545399 A | 12/2008 |
| JP | 2011-511766 A | 4/2011 |
| WO | 2004/100988 A1 | 11/2004 |
| WO | 2006/125195 A2 | 11/2006 |

OTHER PUBLICATIONS

Chen, Ting, et al. "Identification of trypsin-inhibitory site and structure determination of human SPINK2 serine proteinase inhibitor." Proteins: Structure, Function, and Bioinformatics 77.1 (2009): 209-219.*

Luigi R. Ceci, Selection by phage display of a variant mustard trypsin inhibitor toxic against aphids, The Plant Journal (2003) 33, 557-566.*

Extended European Search Report dated Feb. 3, 2016, issued in corresponding International Application No. 13 827 389.1, filed Aug. 7, 2013, 11 pages.

"Hypothetical Protein," UniProt [online] Accession No. Q2TBS5, submitted Nov. 2005 to the EMBL/GenBank/DDBJ databases, <http://www.uniprot.org/uniprot/Q2TBS5.txt?version=2> [retrieved Jan. 24, 2006], 1 page.

Li, Y., et al., "Inhibition Mechanism and the Effects of Structure on Activity of Male Reproduction-Related Peptidase Inhibitor Kazal-Type (MRPINK) of Macrobrachium rosenbergii," Marine Biotechnology 11(2):252-259, Mar.-Apr. 2009.

(Continued)

*Primary Examiner* — Rachael E Bredefeld
*Assistant Examiner* — Erinne R Dabkowski
(74) *Attorney, Agent, or Firm* — Christensen O'Connor Johnson Kindness PLLC

(57) ABSTRACT

Disclosed are compositions and method related to variants of SPINK2 that bind to targets other than an endogenous target of SPINK2. In one embodiment, a peptide is provided that comprises the amino acid sequence SEQ ID NO: 1. In further embodiments, an amino acid sequences encoded by nucleotide positions 4 to 42 and/or nucleotide positions 94 to 189 in the nucleotide sequence of SEQ ID NO: 14 flank the amino terminus and the carboxyl terminus, respectively, of the amino acid sequence. In another embodiment, a peptide is provided that comprises an amino acid sequence derived from the amino acid sequence of SEQ ID NO: 1 in which a conservative substitution, deletion, addition and/or insertion of 1 to 5 (inclusive) amino acids has occurred at amino acids other than the 1st Xaa to the 12th Xaa counting from the amino terminus.

12 Claims, 20 Drawing Sheets

Specification includes a Sequence Listing.

(56) References Cited

OTHER PUBLICATIONS

Perry, A.C., et al., "Acrosin-Trypsin Inhibitor Precursor," UniProt [online] Accession No. P34953, <http://www.uniprot.org/uniprot/P34953.txt?version=1>, [retrieved Feb. 1, 1994], 1 page; reference location: "Sequence Analysis of Monkey Acrosin-Trypsin Inhibitor Transcripts and Their Abundant Expression in the Epididymis," Biochimica et Biophysica Acta 1172(1-2):159-160, Feb. 1993.

Qian, Y.-Q., et al., "Two Kazal-Type Protease Inhibitors From Macrobrachium nipponense and Eriocheir sinensis: Comparitive Analysis of Structure and Activities," Fish & Shellfish Immunology 32(3):446-458, Mar. 2012.

"SubName: Full=Uncharacterized Protein," UniProt [online] Accession No. G1RC24, submitted Jan. 2010 to the EMBL/GenBank/DDBJ databases, <http://www.uniprot.org/uniprot/G1RC24.txt?version=1> [retrieved Oct. 19, 2011], 1 page.

Wilimowska-Pelc, A., et al., "Kazal-Type Chymotrypsin Inhibitor From Duck Pancreas," Comparative Biochemistry and Physiology Part B: Biochemistry and Molecular Biology 131(3):499-507, Mar. 2002.

International Preliminary Report on Patentability dated Feb. 10, 2015, issued in corresponding International Application No. PCT/JP2013/071345, filed Aug. 7, 2013, 17 pages.

International Search Report dated Oct. 29, 2013, issued in corresponding International Application No. PCT/JP2013/071345, filed Aug. 7, 2013, 7 pages.

Chen, T., et al., "Identification of Trypsin-Inhibitory Site and Structure Determination of Human SPINK2 Serine Proteinase Inhibitor," Proteins 77(1):209-219, Oct. 2009.

Communication Pursuant to Article 94(3) EPC, dated Apr. 4, 2017, issued in European Application No. 13827389.1, filed Aug. 7, 2013, 8 pages.

Marks, J.D., et al., "By-Passing Immunization: Human Antibodies From V-Gene Libraries Displayed on Phage," Journal of Molecular Biology 222(3):581-597, Dec. 1991.

Skerra, A., "Alternative Non-Antibody Scaffolds for Molecular Recognition," Current Opinion in Biotechnology 18(4):295-304, Aug. 2007.

Second Communication Pursuant to Article 94(3) EPC, dated Apr. 4, 2018, issued in European Application No. 13827389.1, filed Aug. 7, 2013, 13 pages.

Examination Report dated Apr. 10, 2018, issued in Australian Application No. 2013300549, filed Aug. 7, 2013, 3 pages.

* cited by examiner

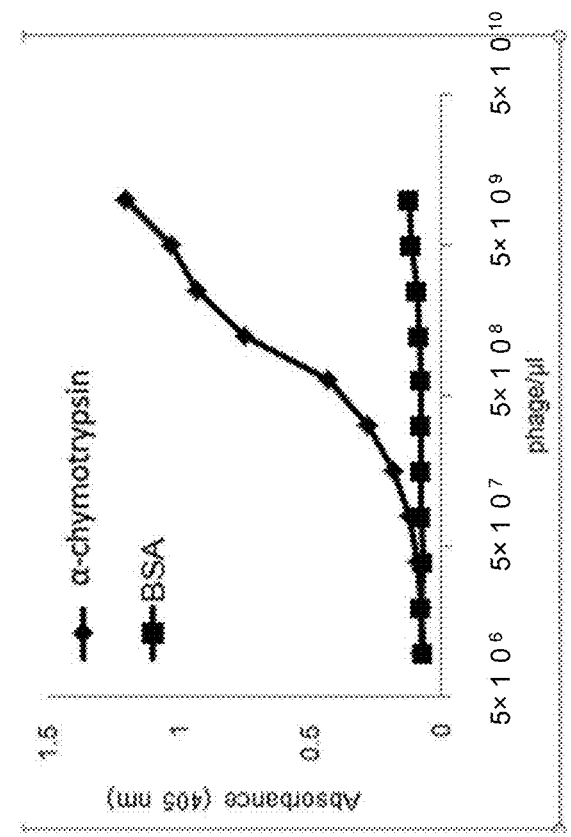
[Figure 1]

[Figure 2]
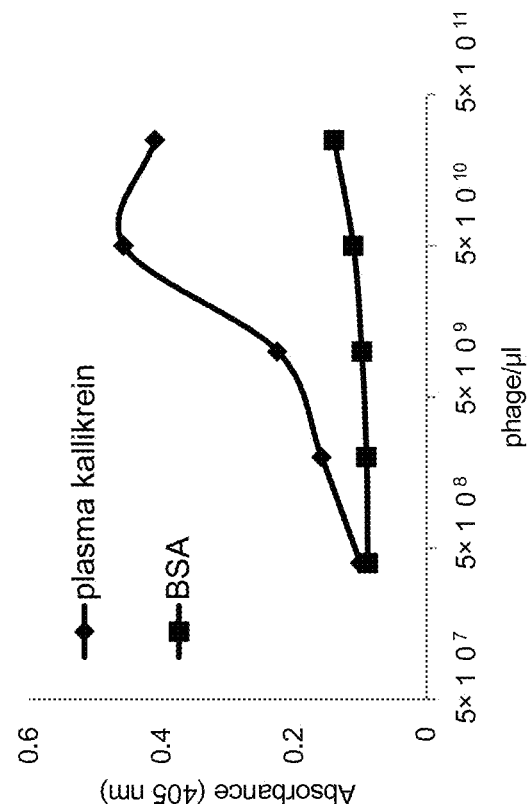

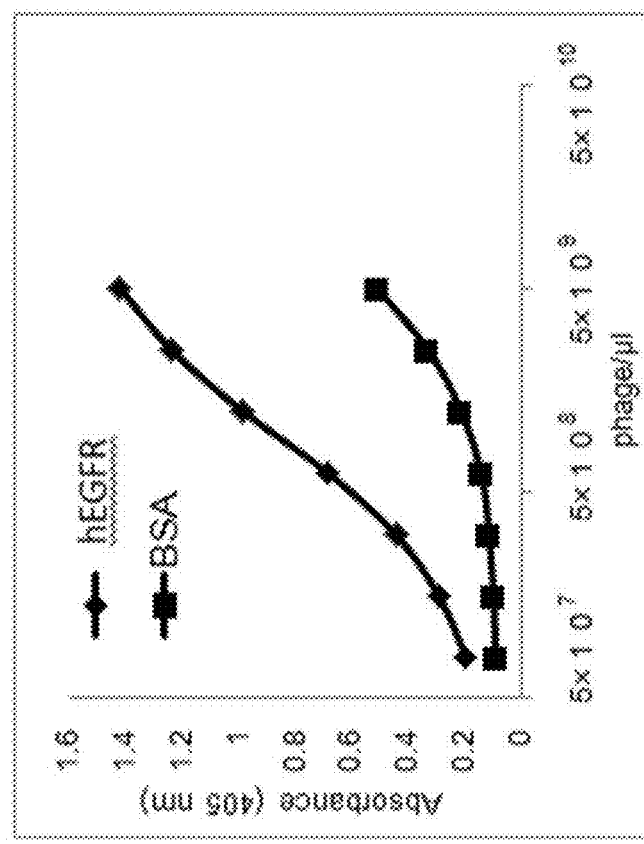
[Figure 3]

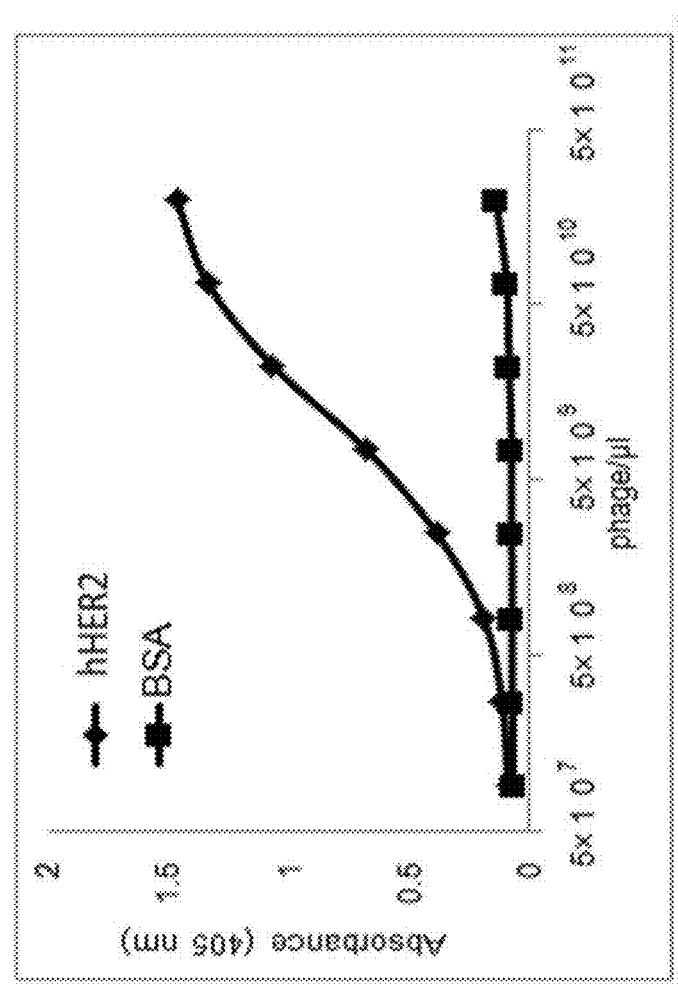
[Figure 4]

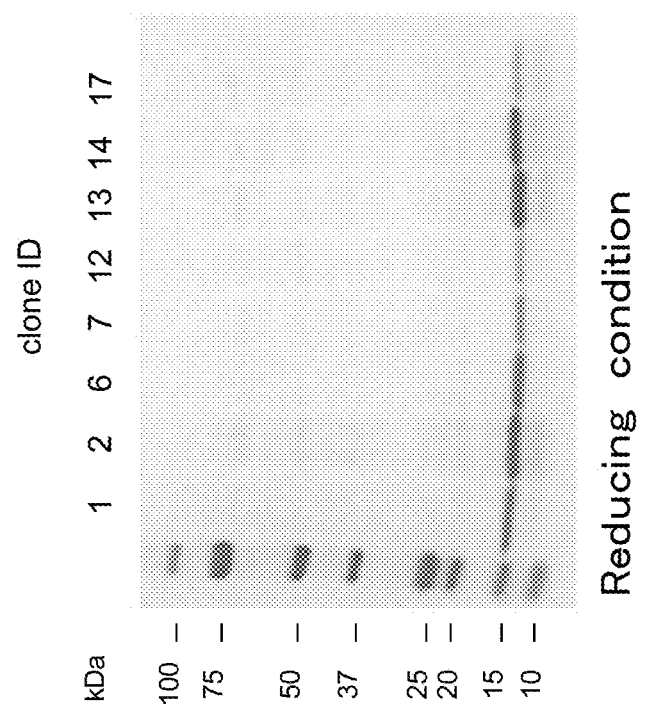
[Figure 5]

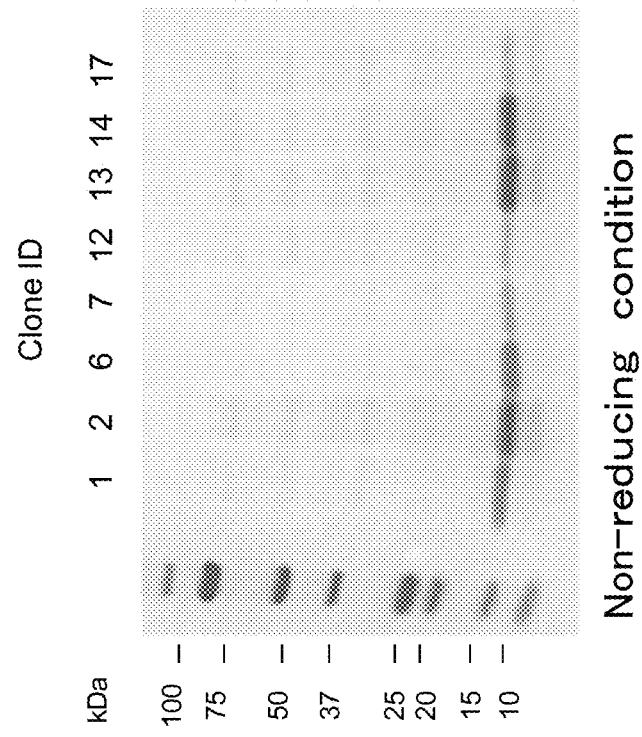
[Figure 6]

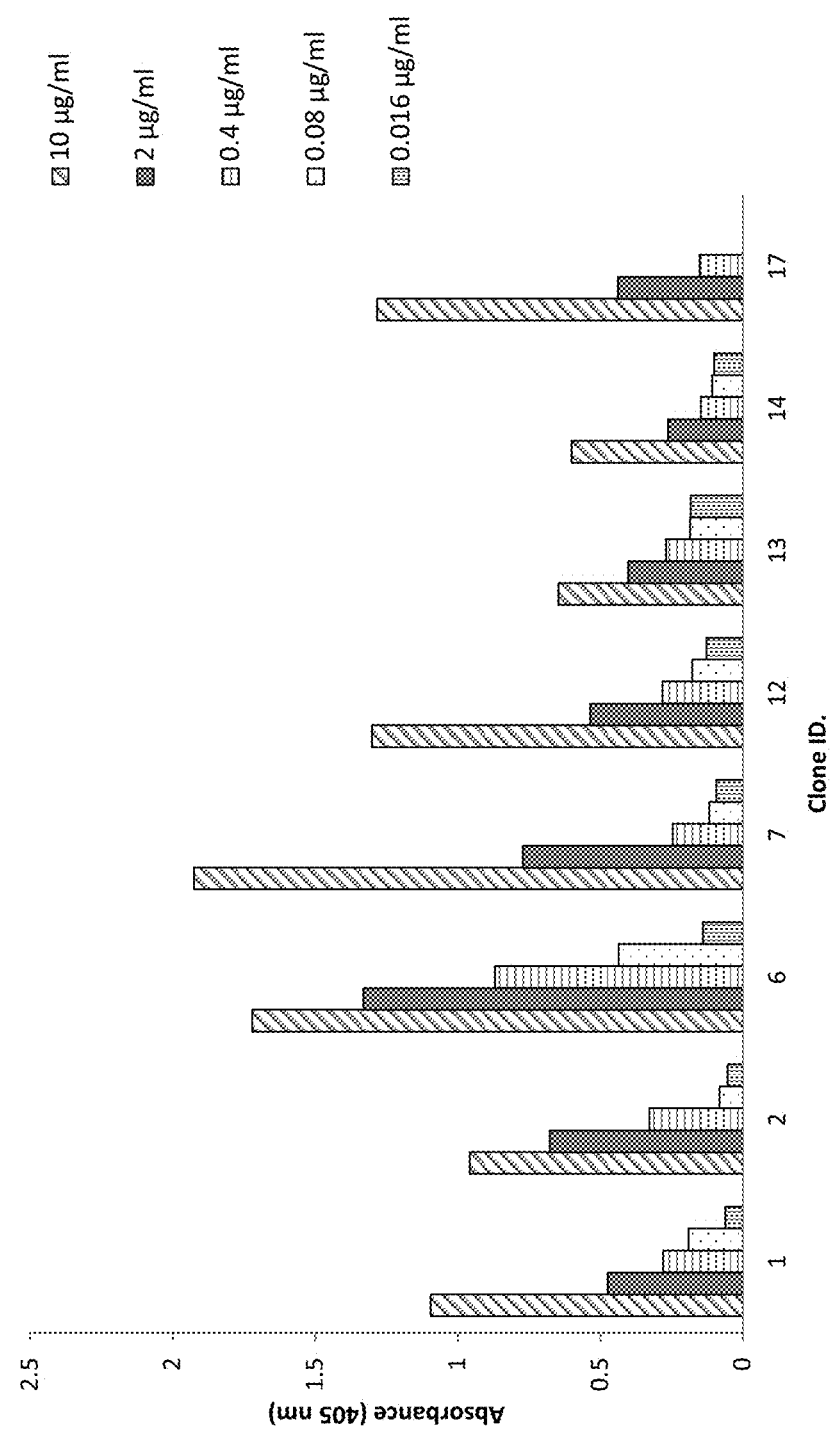
[Figure 7]

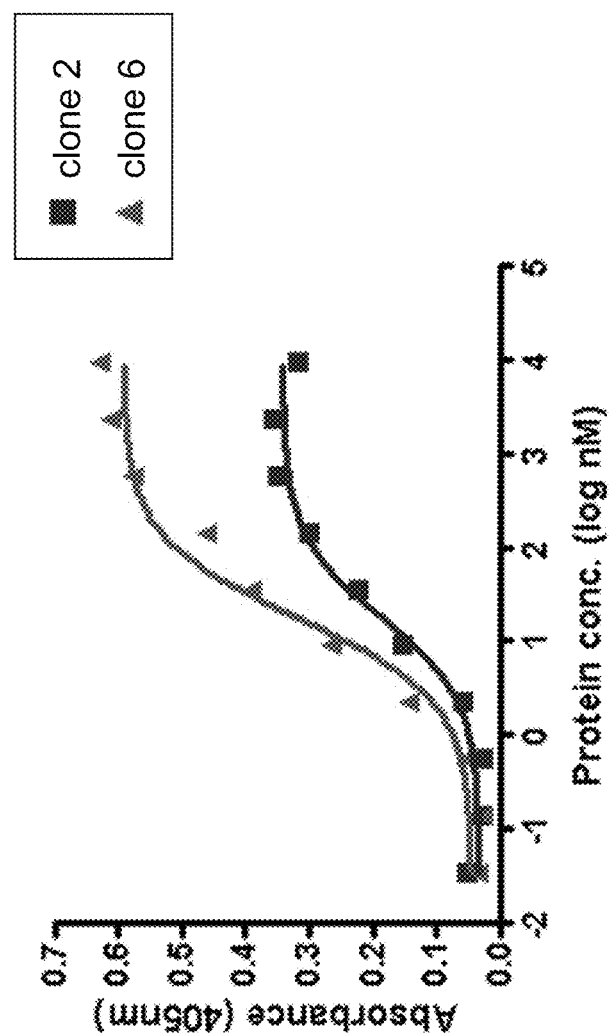
[Figure 8]

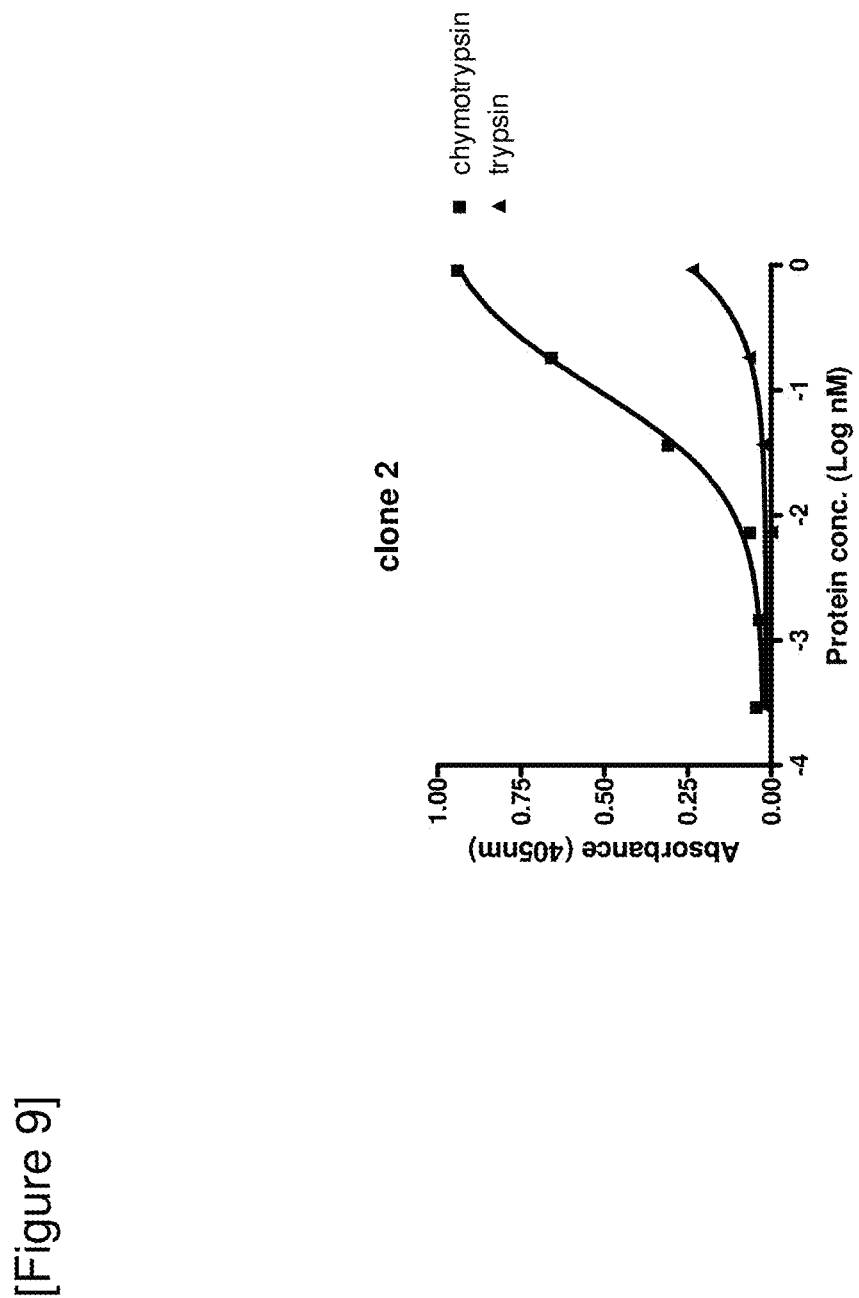
[Figure 9]

[Figure 10]
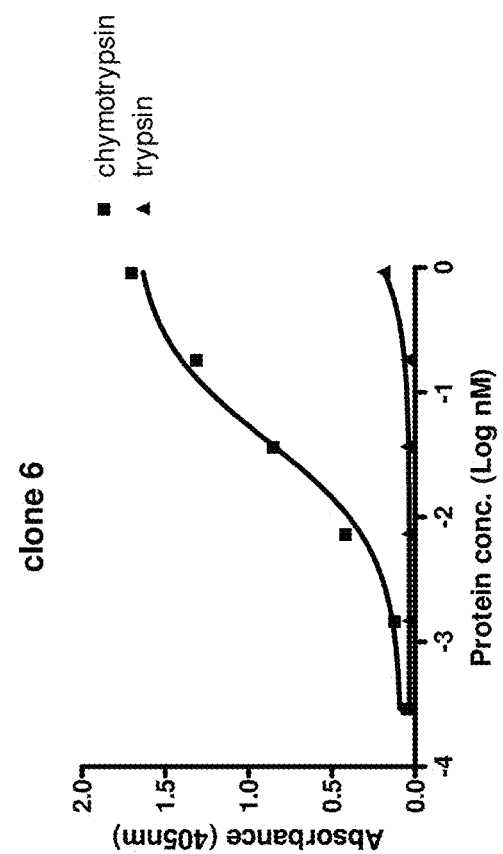

[Figure 11]
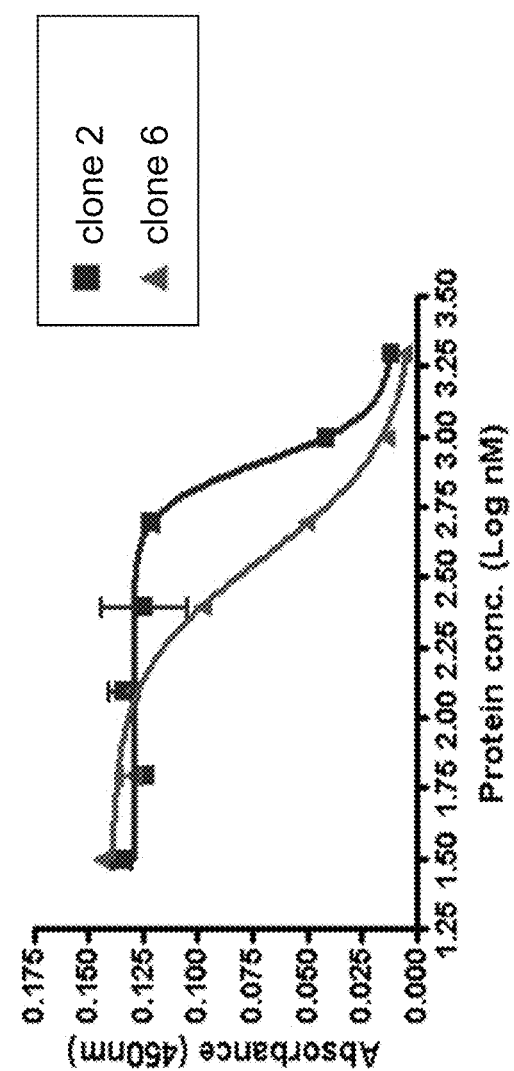

[Figure 12]

| SPINK2 mutant (α-chymotrypsin-binding peptide) | Amino acid sequence |
|---|---|
| Peptide No.1 (SEQ ID No.2) | CRTRW GNRCT WQYKP VC |
| Peptide No.2 (SEQ ID No.3) | CMRHR RHFCT MVYKP VC |
| Peptide No.6 (SEQ ID No.4) | CRRWL LPWCT YKYKP VC |
| Peptide No.7 (SEQ ID No.5) | CLWRR HKLCP FKFKP VC |
| Peptide No.12 (SEQ ID No.6) | CWRSW RWACP YMYKP VC |
| Peptide No.13 (SEQ ID No.7) | CWFFR WRWCN WALKP VC |
| Peptide No.14 (SEQ ID No.8) | CSTWR MWGCP WLYKP VC |
| Peptide No.17 (SEQ ID No.9) | CWRRW YDRCS FNLKP VC |

[Figure 13]

CXXXX XXXCX XXXXP VC (X represents any amino acid)

[Figure 14]

GTACCCGATAAAAGCGGCTTCCTGACAGGAGGCCGTTTTGTTTTGCAGCCCACCT

[Figure 15-1]

```
GACGAAAGGGCCTCGTGATACGCCTATTTTTATAGGTTAATGTCATGATAATAATGG
TTTCTTAGACGTCAGGTGGCACTTTTCGGGGAAATGTGCGCGGAACCCCTATTTGTT
TATTTTTCTAAATACATTCAAATATGTATCCGCTCATGAGACAATAACCCTGATAAA
TGCTTCAATAATATTGAAAAGGAAGAGTATGAGTATTCAACATTTCCGTGTCGCCC
TTATTCCCTTTTTGCGGCATTTTGCCTTCCTGTTTTTGCTCACCCAGAAACGCTGG
TGAAAGTAAAAGATGCTGAAGATCAGTTGGGTGCTCGAGTGGGTTACATCGAACTGG
ATCTCAACAGCGGTAAGATCCTTGAGAGTTTTCGCCCCGAAGAACGTTTTCCAATGA
TGAGCACTTTTAAAGTTCTGCTATGTGGCGCGGTATTATCCCGTATTGACGCCGGGC
AAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTG
CCATAACCATGAGTGATAACACTGCGGCCAACTTACTTCTGACAACGATCGGAGGAC
CGAAGGAGCTAACCGCTTTTTGCACAACATGGGGGATCATGTAACTCGCCTTGATC
GTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAG
CTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGC
GTGGGTCTCGCGGTATCATTGCAGCACTGGGGCCAGATGGTAAGCCCTCCCGTATCG
TAGTTATCTACACGACGGGGAGTCAGGCAACTATGGATGAACGAAATAGACAGATCG
CTGAGATAGGTGCCTCACTGATTAAGCATTGGTAACTGTCAGACCAAGTTTACTCAT
ATATACTTTAGATTGATTTAAAACTTCATTTTTAATT
```

[Figure 15-2]

TAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTG
AGATCCTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGG
CTTCAGCAGAGCGCAGATACCAAATACTGTCCTTCTAGTGTAGCCGTAGTTAGGCCA
CCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCATACAGCCCAG
CTTGGAGCGAACGACCTACACCGAACTGAGATACCTACAGCGTGAGCTATGAGAAAG
CGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCC
TGTCGGGTTTCGCCACCTCTGACTTGAGCGTCGATTTTGTGATGCTCGTCAGGGGG
GCGGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACCG
TATTACCGCCTTTGAGTGAGCTGATACCGCTCGCCGCAGCCGAACGACCGAGCGCAG
CGAGTCAGTGAGCGAGGAAGCGGAAGAGCGCCCAATACGCAAACCGCCTCTCCCCGC
GCGTTGGCCGATTCATTAATGCAGCTGGCACGACAGGTTTCCCGACTGGAAAGCGGG
CAGTGAGCGCAACGCAATTAATGTGAGTTAGCTCACTCATTAGGCACCCCAGGCTTT
ACACTTTATGCTTCCGGCTCGTATGTTGTGTGGAATTGTGAGCGGATAACAATTTCA
CACAGGAAACAGCTATGACCATGATTACGCCAAGCTTGGAGCCTTTTTTTGGAGA
TTTTCAACGTGAAAAAATTATTATTCGCAATTCCTTTAGTTGTTCCTTTCTATGCGG
CCCAGCCGGCCATGGCCCAGGTCCAACTGCAGGTCGACCTCGAGATCAAACGGGCGG
CCGCAGGTGCGCCGGTGCCGTATCCGGATCCGCTGGAACCGCGTGCCGCATAGACTG
TTGAAAGTTGTTTAGCAAAACCTCATACAGAAAATTCATTTACTAACGTCTGGAAAG
ACGACAAAACTTTAGATCGTTACGCTAACTATGAGGGCTGTCTGTGGAATGCTACAG
GCGTTGTGGTTTGTACTGGTGACGAAACTCAGTGTTACGGTACATGGGTTCCTAT

[Figure 15-3]

```
TGGGCTTGCTATCCCTGAAAATGAGGGTGGTGGCTCTGAGGGTGGCGGTTCTGAGGG
TGGCGGTTCTGAGGGTGGCGGTACTAAACCTCCTGAGTACGGTGATACACCTATTCC
GGGCTATACTTATATCAACCCTCTCGACGGCACTTATCCGCCTGGTACTGAGCAAAA
CCCCGCTAATCCTAATCCTTCTCTTGAGGAGTCTCAGCCTCTTAATACTTTCATGTT
TCAGAATAATAGGTTCCGAAATAGGCAGGGTGCATTAACTGTTTATACGGGCACTGT
TACTCAAGGCACTGACCCCGTTAAAACTTATTACCAGTACACTCCTGTATCATCAAA
AGCCATGTATGACGCTTACTGGAACGGTAAATTCAGAGACTGCGCTTTCCATTCTGG
CTTTAATGAGGATCCATTCGTTTGTGAATATCAAGGCCAATCGTCTGACCTGCCTCA
ACCTCCTGTCAATGCTGGCGGCGGCTCTGGTGGTGGTTCTGGTGGCGGCTCTGAGGG
TGGCGGCTCTGAGGGTGGCGGTTCTGAGGGTGGCGGCTCTGAGGGTGGCGGTTCCGG
TGGCGGCTCCGGTTCCGGTGATTTGATTATGAAAAATGGCAAACGCTAATAAGGG
GGCTATGACCGAAAATGCCGATGAAACGCGCTACAGTCTGACGCTAAAGGCAAACT
TGATTCTGTCGCTACTGATTACGGTGCTGCTATCGATGGTTTCATTGGTGACGTTTC
CGGCCTTGCTAATGGTAATGGTGCTACTGGTGATTTGCTGGCTCTAATTCCCAAAT
GGCTCAAGTCGGTGACGGTGATAATTCACCTTTAATGAATAATTTCCGTCAATATTT
ACCTTCTTTGCCTCAGTCGGTTGAATGTCGCCCTTATGTCTTTGGCGCTGGTAAACC
ATATGAATTTTCTATTGATTGTGACAAAATAAACTTATTCCGTGGTGTCTTTGCGTT
TCTTTTATATGTTGCCACCTTTATGTATGTATTTTCGACGTTTGCTAACATACTGCG
TAATAAGGAGTCTTAATAAGAATTCACTGGCCGTCGTTTTACAACGTCGTGACTGGG
AAAACCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAGCCTGA
ATGGCGAATGGCGCCTGATGCGGTATTTCTCCTTACGCATCTGTGCGGTATTTCAC
ACCGCATACGTCAAAGCAACCATAGTACGCGCCCTGTAGCGGCGCATTAAGCGCGGC
GGGTGTGGTGGTTACGCGCAGCGTGACCGCTACACTTGCCAGCGCCCTAGCGCCCGC
TCCTTTCGCTTTCTTCCCTTCCTTTCTCGCCACGTTCGCCGGCTTTCCCCGTCAAGC
TCTAAATCGGGGGCTCCCTTTAGGGTTCCGATTTAGTGCTTTACGGCACCTCGAC
```

[Figure 15-4]

CCCAAAAAACTTGATTTGGGTGATGGTTCACGTAGTGGGCCATCGCCCTGATAGACG

GTTTTTCGCCCTTTGACGTTGGAGTCCACGTTCTTTAATAGTGGACTCTTGTTCCAA

ACTGGAACAACACTCAACCCTATCTCGGGCTATTCTTTTGATTTATAAGGGATTTTG

CCGATTTCGGCCTATTGGTTAAAAATGAGCTGATTTAACAAAATTTAACGCGAAT

TTTAACAAATATTAACGTTTACAATTTTATGGTGCAGTCTCAGTACAATCTGCTCT

GATGCCGCATAGTTAAGCCAGCCCCGACACCCGCCAACACCCGCTGACGCGCCCTGA

CGGGCTTGTCTGCTCCCGGCATCCGCTTACAGACAAGCTGTGACCGTCTCCGGGAGC

TGCATGTGTCAGAGGTTTTCACCGTCATCACCGAAACGCGC

[Figure 16]

AATTTCTAGATAACGAGGGCAAATCATGAAACAAAGCACTATTGCACTGGCACTCTT

ACCGTTGCTGTTTACCCCTGTGACGAAAGCTGCTAGCGCGAATTCtGATCCGCAGTT

TGGTCTGTTTAGCAAATATCGTACCCCGAATTGTAGCCAGTATCGTCTGCCTGGTTG

TCCGCGTCATTTTAATCCGGTTTGTGGTAGCGATATGAGCACCTATGCAAATGAATG

TACCCTGTGCATGAAAATTCGTGAAGGTGGCCATAATATTAAAATTATTCGCAATGG

TCCGTGCgACGCGTCTGCGGCCGC

[Figure 17]

CTGTGAAGTGAAAAATGGCGCACATTGTGCGACATTTTTTTGTCTGCCGTTTAATC

[Figure 18]

GATCCGCAGTTTGGTCTGTTTAGCAAATATCGTACCCCGAATTGTAGCCAGTATCGT

CTGCCTGGTTGTCCGCGTCATTTTAATCCGGTTTGTGGTAGCGATATGAGCACCTAT

GCAAATGAATGTACCCTGTGCATGAAAATTCGTGAAGGTGGCCATAATATTAAAATT

ATTCGCAATGGTCCGTGCTAA

[Figure 19]

DPQFGLFSKYRTPNCSQYRLPGCPRHFNPVCGSDMSTYANECTLCMKIREGGHNIKI
IRNGPC

[Figure 20-1]

GAAGAGCGCCCAATACGCAAACCGCCTCTCCCCGCGCGTTGGCCGATTCATTAATGC

AGCTGGCACGACAGGTTTCCCGACTGGAAAGCGGGCAGTGAGCGGTACCCGATAAAA

GCGGCTTCCTGACAGGAGGCCGTTTTGTTTTGCAGCCCACCTCAACGCAATTAATGT

GAGTTAGCTCACTCATTAGGCACCCCAGGCTTTACACTTTATGCTTCCGGCTCGTAT

GTTGTGTGGAATTGTGAGCGGATAACAATTTCACACAGGAAACAGCTATGACCATGA

TTACGAATTCTAGATAACGAGGGCAAATCATGAAACAAAGCACTATTGCACTGGCA

CTCTTACCGTTGCTGTTTACCCCTGTGACGAAAGCTGCTAGCGCGAATTCtGATCCG

CAGTTTGGTCTGTTTAGCAAATATCGTACCCCGAATTGTAGCCAGTATCGTCTGCCT

GGTTGTCCGCGTCATTTAATCCGGTTTGTGGTAGCGATATGAGCACCTATGCAAAT

GAATGTACCCTGTGCATGAAAATTCGTGAAGGTGGCCATAATATTAAAATTATTCGC

AATGGTCCGTGCgACGCGTCTGCGGCCGCATAGGCAGGTGCATCTGGCGGTGGTTCT

GGCGCAACCGTTGAAAGTTGTTTAGCAAAACCCCATACAGAAAATTCATTTACTAAC

GTCTGGAAAGACGACAAAACTTTAGATCGTTACGCTAACTATGAGGGCTGTCTGTGG

AATGCTACAGGCGTTGTGGTTTGTACTGGTGACGAAACTCAGTGTTACGGTACATGG

GTTCCTATTGGGCTTGCTATCCCTGAAAATGAGGGTGGTGGCTCTGAGGGTGGCGGT

TCTGAGGGTGGCGGTTCTGAGGGTGGCGGTACTAAACCTCCTGAGTACGGTGATACA

CCTATTCCGGGCTATACTTATATCAACCCTCTCGACGGCACTTATCCGCCTGGTACT

GAGCAAAACCCCGCTAATCCTAATCCTTCTCTTGAGGAGTCTCAGCCTCTTAATACT

TTCATGTTTCAGAATAATAGGTTCCGAAATAGGCAGGGTGCATTAACTGTTTATACG

GGCACTGTTACTCAAGGCACTGACCCCGTTAAAACTTATTACCAGTACACTCCTGTA

TCATCAAAAGCCATGTATGACGCTTACTGGAACGGTAAATTCAGAGACTGCGCTTTC

CATTCTGGCTTTAATGAGGATCCATTCGTTTGTGAATATCAAGGCCAATCGTCTGAC

CTGCCTCAACCTCCTGTCAATGCTGG

[Figure 20-2]

CGGCGGCTCTGGTGGTGGTTCTGGTGGCGGCTCTGAGGGTGGCGGCTCTGAGGGTGG

CGGTTCTGAGGGTGGCGGCTCTGAGGGTGGCGGTTCCGGTGGCGGCTCCGGTTCCGG

TGATTTTGATTATGAAAAAATGGCAAACGCTAATAAGGGGGCTATGACCGAAAATGC

CGATGAAAACGCGCTACAGTCTGACGCTAAAGGCAAACTTGATTCTGTCGCTACTGA

TTACGGTGCTGCTATCGATGGTTTCATTGGTGACGTTTCCGGCCTTGCTAATGGTAA

TGGTGCTACTGGTGATTTTGCTGGCTCTAATTCCCAAATGGCTCAAGTCGGTGACGG

TGATAATTCACCTTTAATGAATAATTTCCGTCAATATTTACCTTCTTTGCCTCAGTC

GGTTGAATGTCGCCCTTATGTCTTTGGCGCTGGTAAACCATATGAATTTCTATTGA

TTGTGACAAAATAAACTTATTCCGTGGTGTCTTTGCGTTTCTTTTATATGTTGCCAC

CTTTATGTATGTATTTTCGACGTTTGCTAACATACTGCGTAATAAGGAGTCTTAATA

GTACCTGTGAAGTGAAAAATGGCGCACATTGTGCGACATTTTTTTGTCTGCCGTTT

AATGAATTC

SEQUENCE LISTING

```
<160> NUMBER OF SEQ ID NOS: 35

<210> SEQ ID NO 1
<211> LENGTH: 17
<212> TYPE: PRT
<213> ORGANISM: Artificial Sequence
<220> FEATURE:
<223> OTHER INFORMATION: Peptide with diversity
<220> FEATURE:
<221> NAME/KEY: MISC_FEATURE
<222> LOCATION: (2)..(8)
<223> OTHER INFORMATION: any amino acid
<220> FEATURE:
<221> NAME/KEY: MISC_FEATURE
<222> LOCATION: (10)..(14)
<223> OTHER INFORMATION: any amino acid

<400> SEQUENCE: 1

Cys Xaa Xaa Xaa Xaa Xaa Xaa Xaa Cys Xaa Xaa Xaa Xaa Xaa Pro Val
1               5                   10                  15

Cys

<210> SEQ ID NO 2
<211> LENGTH: 17
<212> TYPE: PRT
<213> ORGANISM: Artificial Sequence
<220> FEATURE:
<223> OTHER INFORMATION: Peptide No.1 binding to alpha-chymotripsin

<400> SEQUENCE: 2
```

```
Cys Arg Thr Arg Trp Gly Asn Arg Cys Thr Trp Gln Tyr Lys Pro Val
1               5                   10                  15

Cys

<210> SEQ ID NO 3
<211> LENGTH: 17
<212> TYPE: PRT
<213> ORGANISM: Artificial Sequence
<220> FEATURE:
<223> OTHER INFORMATION: Peptide No.2 binding to alpha-chymotripsin

<400> SEQUENCE: 3

Cys Met Arg His Arg Arg His Phe Cys Thr Met Val Tyr Lys Pro Val
1               5                   10                  15

Cys

<210> SEQ ID NO 4
<211> LENGTH: 17
<212> TYPE: PRT
<213> ORGANISM: Artificial Sequence
<220> FEATURE:
<223> OTHER INFORMATION: Peptide No.6 binding to alpha-chymotripsin

<400> SEQUENCE: 4

Cys Arg Arg Trp Leu Leu Pro Trp Cys Thr Tyr Lys Tyr Lys Pro Val
1               5                   10                  15

Cys

<210> SEQ ID NO 5
<211> LENGTH: 17
<212> TYPE: PRT
<213> ORGANISM: Artificial Sequence
<220> FEATURE:
<223> OTHER INFORMATION: Peptide No.7 binding to alpha-chymotripsin

<400> SEQUENCE: 5

Cys Leu Trp Arg Arg His Lys Leu Cys Pro Phe Lys Phe Lys Pro Val
1               5                   10                  15

Cys

<210> SEQ ID NO 6
<211> LENGTH: 17
<212> TYPE: PRT
<213> ORGANISM: Artificial Sequence
<220> FEATURE:
<223> OTHER INFORMATION: Peptide No.12 binding to alpha-chymotripsin

<400> SEQUENCE: 6

Cys Trp Arg Ser Trp Arg Trp Ala Cys Pro Tyr Met Tyr Lys Pro Val
1               5                   10                  15

Cys

<210> SEQ ID NO 7
<211> LENGTH: 17
<212> TYPE: PRT
<213> ORGANISM: Artificial Sequence
<220> FEATURE:
<223> OTHER INFORMATION: Peptide No.13 binding to alpha-chymotripsin

<400> SEQUENCE: 7

Cys Trp Phe Phe Arg Trp Arg Trp Cys Asn Trp Ala Leu Lys Pro Val
1               5                   10                  15
```

-continued

Cys

<210> SEQ ID NO 8
<211> LENGTH: 17
<212> TYPE: PRT
<213> ORGANISM: Artificial Sequence
<220> FEATURE:
<223> OTHER INFORMATION: Peptide No.14 binding to alpha-chymotripsin

<400> SEQUENCE: 8

Cys Ser Thr Trp Arg Met Trp Gly Cys Pro Trp Leu Tyr Lys Pro Val
1               5                   10                  15

Cys

<210> SEQ ID NO 9
<211> LENGTH: 17
<212> TYPE: PRT
<213> ORGANISM: Artificial Sequence
<220> FEATURE:
<223> OTHER INFORMATION: Peptide No.17 binding to alpha-chymotripsin

<400> SEQUENCE: 9

Cys Trp Arg Arg Trp Tyr Asp Arg Cys Ser Phe Asn Leu Lys Pro Val
1               5                   10                  15

Cys

<210> SEQ ID NO 10
<211> LENGTH: 55
<212> TYPE: DNA
<213> ORGANISM: Artificial Sequence
<220> FEATURE:
<223> OTHER INFORMATION: Fragment 1

<400> SEQUENCE: 10
gtacccgata aaagcggctt cctgacagga ggccgttttg ttttgcagcc cacct         55

<210> SEQ ID NO 11
<211> LENGTH: 136
<212> TYPE: DNA
<213> ORGANISM: Artificial Sequence
<220> FEATURE:
<223> OTHER INFORMATION: Fragment 2

<400> SEQUENCE: 11
cgcaacgcaa ttaatgtgag ttagctcact cattaggcac cccaggcttt acactttatg    60
cttccggctc gtatgttgtg tggaattgtg agcggataac aatttcacac aggaaacagc   120
tatgaccatg attacg                                                   136

<210> SEQ ID NO 12
<211> LENGTH: 309
<212> TYPE: DNA
<213> ORGANISM: Artificial Sequence
<220> FEATURE:
<223> OTHER INFORMATION: Fragment 3

<400> SEQUENCE: 12
aatttctaga taacgagggc aaatcatgaa acaaagcact attgcactgg cactcttacc    60
gttgctgttt acccctgtga cgaaagctgc tagcgcgaat tctgatccgc agtttggtct   120
gtttagcaaa tatcgtaccc cgaattgtag ccagtatcgt ctgcctggtt gtccgcgtca   180
ttttaatccg gtttgtggta gcgatatgag cacctatgca aatgaatgta ccctgtgcat   240
gaaaattcgt gaaggtggcc ataatattaa aattattcgc aatggtccgt gcgacgcgtc   300
tgcggccgc                                                         309

<210> SEQ ID NO 13
<211> LENGTH: 57
<212> TYPE: DNA
<213> ORGANISM: Artificial Sequence
<220> FEATURE:
<223> OTHER INFORMATION: Fragment 5

<400> SEQUENCE: 13
ctgtgaagtg aaaaatggcg cacattgtgc gacattttt ttgtctgccg tttaatc     57

<210> SEQ ID NO 14
<211> LENGTH: 192
<212> TYPE: DNA
<213> ORGANISM: Homo sapiens
<220> FEATURE:
<221> NAME/KEY: CDS
<222> LOCATION: (1)..(192)

<400> SEQUENCE: 14 gat ccg cag ttt ggt ctg ttt agc aaa tat cgt acc ccg aat tgt agc     48
Asp Pro Gln Phe Gly Leu Phe Ser Lys Tyr Arg Thr Pro Asn Cys Ser
1               5                   10                  15 cag tat cgt ctg cct ggt tgt ccg cgt cat ttt aat ccg gtt tgt ggt     96
Gln Tyr Arg Leu Pro Gly Cys Pro Arg His Phe Asn Pro Val Cys Gly
            20                  25                  30 agc gat atg agc acc tat gca aat gaa tgt acc ctg tgc atg aaa att    144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc taa    192
Arg Glu Gly Gly His Asn Ile Lys Ile Ile Arg Asn Gly Pro Cys
    50                  55                  60

<210> SEQ ID NO 15
<211> LENGTH: 63
<212> TYPE: PRT
<213> ORGANISM: Homo sapiens

<400> SEQUENCE: 15

Asp Pro Gln Phe Gly Leu Phe Ser Lys Tyr Arg Thr Pro Asn Cys Ser
1               5                   10                  15

Gln Tyr Arg Leu Pro Gly Cys Pro Arg His Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 16
<211> LENGTH: 1916
<212> TYPE: DNA
<213> ORGANISM: Artificial
<220> FEATURE:
<223> OTHER INFORMATION: A template DNA for PCR comprising Fragments 1
      to 5

<400> SEQUENCE: 16
gaagagcgcc caatacgcaa accgcctctc ccgcgcgtt ggccgattca ttaatgcagc     60
tggcacgaca ggtttcccga ctggaaagcg ggcagtgagc ggtacccgat aaaagcggct   120
tcctgacagg aggccgtttt gttttgcagc ccacctcaac gcaattaatg tgagttagct   180

```
cactcattag gcaccccagg ctttacactt tatgcttccg gctcgtatgt tgtgtggaat      240
tgtgagcgga taacaatttc acacaggaaa cagctatgac catgattacg aatttctaga      300
taacgagggc aaatcatgaa acaaagcact attgcactgg cactcttacc gttgctgttt      360
acccctgtga cgaaagctgc tagcgcgaat tctgatccgc agtttggtct gtttagcaaa      420
tatcgtaccc cgaattgtag ccagtatcgt ctgcctggtt gtccgcgtca ttttaatccg      480
gtttgtggta gcgatatgag cacctatgca aatgaatgta ccctgtgcat gaaaattcgt      540
gaaggtggcc ataatattaa aattattcgc aatggtccgt gcgacgcgtc tgcggccgca      600
taggcaggtg catctggcgg tggttctggc gcaaccgttg aaagttgttt agcaaaaccc      660
catacagaaa attcatttac taacgtctgg aaagacgaca aaactttaga tcgttacgct      720
aactatgagg gctgtctgtg gaatgctaca ggcgttgtgg tttgtactgg tgacgaaact      780
cagtgttacg gtacatgggt tcctattggg cttgctatcc ctgaaaatga gggtggtggc      840
tctgagggtg gcggttctga gggtggcggt tctgagggtg gcggtactaa acctcctgag      900
tacggtgata cacctattcc gggctatact tatatcaacc ctctcgacgg cacttatccg      960
cctggtactg agcaaaaccc cgctaatcct aatccttctc ttgaggagtc tcagcctctt     1020
aatactttca tgtttcagaa taataggttc gaaataggc agggtgcatt aactgtttat     1080
acgggcactg ttactcaagg cactgacccc gttaaaactt attaccagta cactcctgta     1140
tcatcaaaag ccatgtatga cgcttactgg aacggtaaat tcagagactg cgctttccat     1200
tctggcttta atgaggatcc attcgtttgt gaatatcaag gccaatcgtc tgacctgcct     1260
caacctcctg tcaatgctgg cggcggctct ggtggtggtt ctggtggcgg ctctgagggt     1320
ggcggctctg agggtggcgg ttctgagggt ggcggctctg agggtggcgg ttccggtggc     1380
ggctccggtt ccggtgattt tgattatgaa aaaatggcaa acgctaataa gggggctatg     1440
accgaaaatg ccgatgaaaa cgcgctacag tctgacgcta aaggcaaact tgattctgtc     1500
gctactgatt acggtgctgc tatcgatggt ttcattggtg acgtttccgg ccttgctaat     1560
ggtaatggtg ctactggtga ttttgctggc tctaattccc aaatggctca agtcggtgac     1620
ggtgataatt caccttttaat gaataatttc cgtcaatatt accttctttt gcctcagtcg     1680
gttgaatgtc gcccttatgt ctttggcgct ggtaaaccat atgaatttc tattgattgt     1740 gacaaaataa acttattccg tggtgtcttt gcgtttcttt tatatgttgc cacctttatg     1800
tatgtatttt cgacgtttgc taacatactg cgtaataagg agtcttaata gtacctgtga     1860
agtgaaaaat ggcgcacatt gtgcgacatt tttttgtct gccgtttaat gaattc         1916
```

<210> SEQ ID NO 17
<211> LENGTH: 39
<212> TYPE: DNA
<213> ORGANISM: Artificial Sequence
<220> FEATURE:
<223> OTHER INFORMATION: Primer 1

<400> SEQUENCE: 17
aaaaaacgcg tctgcggccg catagggtag cgaaaacct                              39

<210> SEQ ID NO 18
<211> LENGTH: 40
<212> TYPE: DNA
<213> ORGANISM: Artificial Sequence
<220> FEATURE:
<223> OTHER INFORMATION: Primer 2

<400> SEQUENCE: 18
aaaaaggcgc cattcgccat tcaggctgcg caactgttgg                                      40

<210> SEQ ID NO 19
<211> LENGTH: 35
<212> TYPE: DNA
<213> ORGANISM: Artificial Sequence
<220> FEATURE:
<223> OTHER INFORMATION: Primer 1'

<400> SEQUENCE: 19
aaaagaagag cgcccaatac gcaaaccgcc tctcc                                           35

<210> SEQ ID NO 20
<211> LENGTH: 39
<212> TYPE: DNA
<213> ORGANISM: Artificial Sequence
<220> FEATURE:
<223> OTHER INFORMATION: Primer 2'

<400> SEQUENCE: 20 aaaagaatt cattaaacgg cagacaaaaa aaatgtcgc                                        39

<210> SEQ ID NO 21
<211> LENGTH: 38
<212> TYPE: DNA
<213> ORGANISM: Artificial Sequence
<220> FEATURE:
<223> OTHER INFORMATION: Primer 3

<400> SEQUENCE: 21
gcggccgcat agggtagcga aaacctgtat tttcagag                                        38

<210> SEQ ID NO 22
<211> LENGTH: 42
<212> TYPE: DNA
<213> ORGANISM: Artificial Sequence
<220> FEATURE:
<223> OTHER INFORMATION: Primer 4

<400> SEQUENCE: 22
gctaaacaac tttcaacggt gctaccgctc tgaaaataca gg                                   42

<210> SEQ ID NO 23
<211> LENGTH: 27
<212> TYPE: DNA
<213> ORGANISM: Artificial Sequence
<220> FEATURE:
<223> OTHER INFORMATION: Primer 5

<400> SEQUENCE: 23
accgttgaaa gttgtttagc aaaaccc                                                    27

<210> SEQ ID NO 24
<211> LENGTH: 28
<212> TYPE: DNA
<213> ORGANISM: Artificial Sequence
<220> FEATURE:
<223> OTHER INFORMATION: Primer 6

<400> SEQUENCE: 24
cattaaagcc agaatggaaa gcgcagtc                                                   28

<210> SEQ ID NO 25
<211> LENGTH: 29
<212> TYPE: DNA

```
<213> ORGANISM: Artificial Sequence
<220> FEATURE:
<223> OTHER INFORMATION: Primer alpha

<400> SEQUENCE: 25
aacacgcgtc tgcggccgca tagggtagc                                    29

<210> SEQ ID NO 26
<211> LENGTH: 31
<212> TYPE: DNA
<213> ORGANISM: Artificial Sequence
<220> FEATURE:
<223> OTHER INFORMATION: Primer beta

<400> SEQUENCE: 26
aacggatcct cattaaagcc agaatggaaa g                                 31

<210> SEQ ID NO 27
<211> LENGTH: 23
<212> TYPE: DNA
<213> ORGANISM: Artificial Sequence
<220> FEATURE:
<223> OTHER INFORMATION: Primer 7

<400> SEQUENCE: 27
ggtagcgata tgagcaccta tgc                                          23

<210> SEQ ID NO 28
<211> LENGTH: 19
<212> TYPE: DNA
<213> ORGANISM: Artificial Sequence
<220> FEATURE:
<223> OTHER INFORMATION: Primer 8

<400> SEQUENCE: 28
gcacggacca ttgcgaata                                               19

<210> SEQ ID NO 29
<211> LENGTH: 37
<212> TYPE: DNA
<213> ORGANISM: Artificial Sequence
<220> FEATURE:
<223> OTHER INFORMATION: Primer 9

<400> SEQUENCE: 29
gtttggtctg tttagcaaat atcgtacccc gaattgt                           37

<210> SEQ ID NO 30
<211> LENGTH: 19
<212> TYPE: DNA
<213> ORGANISM: Artificial Sequence
<220> FEATURE:
<223> OTHER INFORMATION: Primer 10

<400> SEQUENCE: 30
gcacggacca ttgcgaata                                               19

<210> SEQ ID NO 31
<211> LENGTH: 44
<212> TYPE: DNA
<213> ORGANISM: Artificial Sequence
<220> FEATURE:
<223> OTHER INFORMATION: Primer 11

<400> SEQUENCE: 31
aaagaattct gatccgcagt tggtctgtt tagcaaataa tcgt                    44
```

```
<210> SEQ ID NO 32
<211> LENGTH: 38
<212> TYPE: DNA
<213> ORGANISM: Artificial Sequence
<220> FEATURE:
<223> OTHER INFORMATION: Primer 12

<400> SEQUENCE: 32
aaaggcgcgc cgcacggacc attgcgaata attttaat                              38

<210> SEQ ID NO 33
<211> LENGTH: 37
<212> TYPE: DNA
<213> ORGANISM: Artificial Sequence
<220> FEATURE:
<223> OTHER INFORMATION: Primer 13

<400> SEQUENCE: 33
aaaggatccg cgaattcatg accgagtaca agcccac                               37

<210> SEQ ID NO 34
<211> LENGTH: 40
<212> TYPE: DNA
<213> ORGANISM: Artificial Sequence
<220> FEATURE:
<223> OTHER INFORMATION: Primer 14

<400> SEQUENCE: 34
aaactcgagt tatgcggccg ctcaggcacc gggcttgcgg                            40

<210> SEQ ID NO 35
<211> LENGTH: 27
<212> TYPE: DNA
<213> ORGANISM: Artificial Sequence
<220> FEATURE:
<223> OTHER INFORMATION: Primer 15

<400> SEQUENCE: 35
gttctggttc tggccatatg caccatc                                          27
```

PEPTIDE LIBRARY AND USE THEREOF

TECHNICAL FIELD

The present invention relates to a peptide, a derivative of the peptide, a nucleic acid corresponding to the peptide or the derivative of the peptide, a vector comprising the nucleic acid, a cell in which the vector and/or the nucleic acid is introduced, a method for producing the peptide and/or the derivative thereof comprising culturing the cell, a peptide library comprising the peptide and/or the derivative thereof, a method for identifying a peptide and/or a derivative thereof binding to a target molecule, a method for producing a peptide and/or a derivative thereof that binds to a target molecule, a method for determining whether or not a test peptide and/or derivative thereof binds to a target molecule, a nucleic acid library comprising the nucleic acid, a composition comprising the peptide or the derivative thereof, the nucleic acid, the vector, or the cell, a reagent comprising the peptide or the derivative thereof, the nucleic acid, the vector, or the cell, etc.

BACKGROUND ART

SPINK2 (serine protease inhibitor Kazal-type 2) is a 7 kDa protein composed of Kazal-type domains having three disulfide bonds. In the human body, this protein is expressed in the testis or the seminal vesicle and functions as a trypsin/acrosin inhibitor (Non Patent Literature 1).

In 1991, Winter et al., reported antibody screening using phage display, and this phage display had a great impact on the development of antibody drugs by providing a method for developing fully human antibodies (Non Patent Literature 2). With recent advances in protein engineering, non-antibody scaffolds have been increasingly actively developed using display techniques such as phage display or ribosome display. These non-antibody scaffolds, also called engineering binding (affinity) proteins, etc., refer to artificial proteins provided with antibody variable region (CDR)-like binding regions. The non-antibody scaffolds have binding activity against protein X to be targeted and permit protein-protein interaction. In addition, the non-antibody scaffolds have beneficial characteristics from the viewpoint of productivity, immunogenicity, tissue infiltration, etc. As typified by Kunitz domain library (Dyax Corp.) (Patent Literature 1), anticalin (Pieris AG), or the like, only limited types of non-antibody scaffolds have been developed, though their scientific or industrial rise has been desired. Thus, the development of a novel non-antibody scaffold against a disease-related molecule has been desired (Non Patent Literature 3).

CITATION LIST

Patent Literature

Patent Literature 1: U.S. Patent Application Publication No. US2008/0020394 A1 (or Japanese National Publication of International Patent Application Publication No. 2007-524348)

Non Patent Literature

Non Patent Literature 1: Chen T, Lee T R, Liang W G, Chang W S, Lyu P C. (2009) Identification of trypsin-inhibitory site and structure determination of human SPINK2 serine proteinase inhibitor. Proteins. 77 (1):209-19.

Non Patent Literature 2: James D. Marks, Hennie R. Hoogenboom, Timothy P. Bonnert, John McCafferty, Andrew D. Griffiths, Greg Winter (1991) By-passing immunization: Human antibodies from V-gene libraries displayed on phage. J Mol Biol. 222(3):581-97.

Non Patent Literature 3: Skerra A. (2007) Alternative non-antibody scaffolds for molecular recognition. Curr Opin Biotechnol. 18:295-304.

SUMMARY OF INVENTION

Technical Problem

The present inventors have conducted diligent studies on SPINK2 and a variant thereof, and consequently completed the present invention, for example, by preparing a library comprising a peptide that exhibits high binding activity against a molecule other than an endogenous target of SPINK2 and isolating, from the library, a peptide that exhibits high binding activity against a target molecule other than the endogenous target.

Solution to Problem

The present invention relates to:

(1)
a peptide selected from the following (i) and (ii):
(i) a peptide comprising an amino acid sequence encoded by a nucleotide sequence derived from SEQ ID NO: 14 in the Sequence Listing by replacing a nucleotide sequence consisting of the 43rd base thymine to the 93rd base thymine with a nucleotide sequence encoding the amino acid sequence represented by SEQ ID NO: 1 in the Sequence Listing; and
(ii) the peptide according to (i) having an amino acid sequence derived from the amino acid sequence represented by SEQ ID NO: 1 in the Sequence Listing by the amino acid substitution, deletion, addition, and/or insertion of 1 to 5 (inclusive) amino acids except at amino acid positions 2 to 8 and 10 to 14;

(2)
the peptide according to (1), wherein each of the 1st Xaa to the 5th Xaa, the 7th Xaa, the 9th Xaa, and the 10th Xaa counting from the amino terminus of SEQ ID NO: 1 in the Sequence Listing is any amino acid other than cysteine and proline;

(3)
the peptide according to (1) or (2), wherein each of the 6th Xaa and the 8th Xaa counting from the amino terminus of SEQ ID NO: 1 in the Sequence Listing is any amino acid other than cysteine;

(4)
the peptide according to any one of (1) to (3), wherein the 11th Xaa counting from the amino terminus of SEQ ID NO: 1 in the Sequence Listing is an amino acid selected from the group consisting of tyrosine, serine, phenylalanine, leucine, and threonine;

(5)
the peptide according to any one of (1) to (4), wherein the 12th Xaa counting from the amino terminus of SEQ ID NO: 1 in the Sequence Listing is an amino acid selected from the group consisting of asparagine, aspartic acid, leucine, lysine, glutamine, alanine, and glutamic acid;

(6)
the peptide according to any one of (1) to (5), wherein the amino acid substitution is a conservative amino acid substitution which occurs within any group selected from a hydrophobic amino acid group, a neutral hydrophilic amino acid group, an acidic amino acid group, a basic amino acid group, a group of amino acids influencing the direction of the main chain, and an aromatic amino acid group;

(7)
the peptide according to any one of (1) to (6), wherein the 1st Xaa counting from the amino terminus of SEQ ID NO: 1 in the Sequence Listing is an amino acid selected from the group consisting of arginine, methionine, leucine, tryptophan, and serine;

(8)
the peptide according to any one of (1) to (7), wherein the 2nd Xaa counting from the amino terminus of SEQ ID NO: 1 in the Sequence Listing is an amino acid selected from the group consisting of threonine, arginine, tryptophan, and phenylalanine;

(9)
the peptide according to any one of (1) to (8), wherein the 3rd Xaa counting from the amino terminus of SEQ ID NO: 1 in the Sequence Listing is an amino acid selected from the group consisting of arginine, histidine, tryptophan, serine, and phenylalanine;

(10)
the peptide according to any one of (1) to (9), wherein the 4th Xaa counting from the amino terminus of SEQ ID NO: 1 in the Sequence Listing is an amino acid selected from the group consisting of tryptophan, arginine, and leucine;

(11)
the peptide according to any one of (1) to (10), wherein the 5th Xaa counting from the amino terminus of SEQ ID NO: 1 in the Sequence Listing is an amino acid selected from the group consisting of glycine, arginine, leucine, histidine, tryptophan, methionine, and tyrosine;

(12)
the peptide according to any one of (1) to (11), wherein the 6th Xaa counting from the amino terminus of SEQ ID NO: 1 in the Sequence Listing is an amino acid selected from the group consisting of asparagine, histidine, proline, lysine, tryptophan, arginine, and aspartic acid;

(13)
the peptide according to any one of (1) to (12), wherein the 7th Xaa counting from the amino terminus of SEQ ID NO: 1 in the Sequence Listing is an amino acid selected from the group consisting of arginine, phenylalanine, tryptophan, leucine, alanine, and glycine;

(14)
the peptide according to any one of (1) to (13), wherein the 8th Xaa counting from the amino terminus of SEQ ID NO: 1 in the Sequence Listing is an amino acid selected from the group consisting of threonine, proline, asparagine, and serine; (15) the peptide according to any one of (1) to (14), wherein the 9th Xaa counting from the amino terminus of SEQ ID NO: 1 in the Sequence Listing is an amino acid selected from the group consisting of tryptophan, methionine, tyrosine, and phenylalanine;

(16)
the peptide according to any one of (1) to (15), wherein the 10th Xaa counting from the amino terminus of SEQ ID NO: 1 in the Sequence Listing is an amino acid selected from the group consisting of glutamine, valine, lysine, methionine, alanine, leucine, and asparagine;

(17)
the peptide according to any one of (1) to (16), wherein the 11th Xaa counting from the amino terminus of SEQ ID NO: 1 in the Sequence Listing is an amino acid selected from the group consisting of tyrosine, phenylalanine, and leucine;

(18)
the peptide according to any one of (1) to (17), wherein the 12th Xaa counting from the amino terminus of SEQ ID NO: 1 in the Sequence Listing is lysine;

(19)
the peptide according to any one of (1) to (18), wherein the peptide comprises the amino acid sequence represented by any one of SEQ ID NOs: 2 to 9 in the Sequence Listing (peptide Nos. 1, 2, 6, 7, 12 to 14, and 17 in FIG. 12);

(20)
a derivative of a peptide according to any one of (1) to (19), the derivative being prepared by chemically modifying and/or biologically modifying the peptide;

(21)
a nucleic acid described in any one of the following (i) to (iii):
(i) a nucleic acid comprising a nucleic acid consisting of a nucleotide sequence encoding the amino acid sequence of a peptide according to any one of (1) to (19);
(ii) a nucleic acid comprising a nucleotide sequence encoding the amino acid sequence of a peptide according to any one of (1) to (19); and
(iii) a nucleic acid consisting of a nucleotide sequence encoding the amino acid sequence of a peptide according to any one of (1) to (19);

(22)
a vector comprising the nucleic acid according to (21);

(23)
a cell in which the nucleic acid according to (21) or a vector according to (22) is introduced;

(24)
a method for producing the peptide according to any one of (1) to (19), comprising the following steps (i) and (ii):
(i) culturing a cell according to (23); and
(ii) recovering the peptide from the culture obtained in step (i);

(25)
a peptide library comprising a peptide according to any one of (1) to (19) and/or a peptide derivative according to (20);

(26)
the library according to (25), wherein the peptide and/or the peptide derivative are prepared by a method comprising steps (i) and (ii) according to (24);

(27)
the library according to (25) or (26), wherein in the library, the peptide or the peptide derivative as a phenotype is linked directly or indirectly to a nucleic acid as a genotype corresponding to the phenotype;

(28)
the library according to (27), wherein the nucleic acid is the nucleic acid according to (21);

(29)
the library according to any one of (25) to (28), wherein the library is a phage display library, a ribosome display library, or a nucleic acid display library;

(30)
a method for identifying the peptide according to any one of (1) to (19) or a peptide derivative according to (20) that binds to a target molecule, comprising the following steps (i) and (ii):

(i) contacting peptides or peptide derivatives contained in a library according to any one of (25) to (29) with the target molecule; and
(ii) recovering a peptide or a peptide derivative that binds to the target molecule;
(31)
a method for producing the peptide according to any one of (1) to (19) or a peptide derivative according to (20) that binds to a target molecule, comprising the following steps (i) to (iii):
(i) contacting peptides or peptide derivatives contained in a library according to any one of (25) to (29) with the target molecule;
(ii) recovering a peptide or a peptide derivative that binds to the target molecule; and
(iii) preparing, by chemical synthesis, gene recombination, or in vitro translation, a peptide binding to the target molecule, wherein said peptide corresponds to the peptide or is contained in the peptide derivative recovered in step (ii);
(32)
a method for determining whether or not the peptide according to any one of (1) to (19) or the peptide derivative according to (20) binds to a target molecule, comprising the following steps (i) and (ii):
(i) contacting test peptides according to any one of (1) to (19) or test peptide derivatives according to (20) with the target molecule; and
(ii) determining that the test peptide or the test peptide derivative is positive for binding, when the test peptide or the test peptide derivative binds to the target molecule;
(33)
a method for producing the peptide according to any one of (1) to (19) or the peptide derivative according to (20) that binds to a target molecule, comprising the following steps (i) to (iii):
(i) contacting test peptides according to any one of (1) to (19) or test peptide derivatives according to (20) with the target molecule;
(ii) determining that the test peptide or the test peptide derivative is positive for binding, when the test peptide or the test peptide derivative binds to the target molecule; and
(iii) when the test peptide or peptide derivative has been determined to be positive in step (ii), preparing a peptide that binds to the target molecule by gene recombination or in vitro translation, wherein said peptide corresponds to the peptide or is contained in the peptide derivative;
(34)
a nucleic acid library comprising the nucleic acid according to (21);
(35)
the library according to (34), wherein the nucleic acid is present in a phagemid, a cosmid, or a plasmid, or a fragment thereof;
(36)
the nucleic acid library according to (34) or (35), wherein the nucleic acid is present in a prokaryotic or eukaryotic cell, on viral DNA or RNA, or in a viral particle;
(37)
a composition comprising the peptide according to any one of (1) to (19), the peptide derivative according to (20), the nucleic acid according to (21), the vector according to (22), or the cell according to (23).
(38)
a reagent comprising the peptide according to any one of (1) to (19), the peptide derivative according to (20), the nucleic acid according to (21), the vector according to (22), or the cell according to (23); (39)
the peptide according to any one of (1) to (19) or the peptide derivative according to (20) that binds to a predetermined target molecule;
(40)
the peptide or the peptide derivative according to (39), wherein the target molecule is not an endogenous target of SPINK2;
(41)
the peptide or the peptide derivative according to (39) or (40), wherein the target molecule is derived from a human;
(42)
the peptide or the peptide derivative according to any one of (39) to (41), wherein the endogenous target is trypsin and/or acrosin;
(43)
the peptide or the peptide derivative according to any one of (39) to (42), wherein the endogenous target is trypsin;
(44)
a composition or a reagent comprising the peptide or the peptide derivative according to any one of (39) to (43);
(45)
a method for identifying the peptide according to any one of (1) to (19) or the peptide derivative according to (20) that binds to a serine protease other than trypsin and/or acrosin and inhibits the proteolytic activity of the serine protease (peptide bond hydrolytic activity; the same holds true for the description below) comprising the following steps (i) to (iii):
(i) contacting peptides or peptide derivatives contained in a library according to any one of (25) to (29) with the serine protease;
(ii) recovering a peptide or a peptide derivative that binds to the serine protease; and
(iii) determining that the peptide or the peptide derivative is positive for inhibition, when the peptide or the peptide derivative inhibits the proteolytic activity of the serine protease;
(46)
a method for producing the peptide according to any one of (1) to (19) or the peptide derivative according to (20) that binds to a serine protease other than trypsin and/or acrosin and inhibits the proteolytic activity of the serine protease, comprising the following steps (i) to (iv):
(i) contacting peptides or peptide derivatives contained in a library according to any one of (25) to (29) with the serine protease;
(ii) recovering a peptide or a peptide derivative that binds to the serine protease;
(iii) determining that the peptide or the peptide derivative is positive for inhibition, when the peptide or the peptide derivative recovered in step (ii) inhibits the proteolytic activity of the serine protease; and
(iv) preparing, by chemical synthesis, gene recombination, or in vitro translation, a peptide inhibiting the proteolytic activity of the serine protease, wherein said peptide corresponds to the peptide or is contained in the peptide derivative determined to be positive in step (iii);
(47)
a method for determining whether or not the peptide according to any one of (1) to (19) or the peptide derivative according to (20) inhibits the proteolytic activity of a serine protease other than trypsin and/or acrosin (peptide bond hydrolytic activity; the same holds true for the description below), comprising the following steps (i) and (ii):
(i) contacting test peptides according to any one of (1) to (19) or test peptide derivatives according to (20) with the serine protease; and (ii) determining that the peptide or the peptide derivative is positive for inhibition, when the peptide or the peptide derivative inhibits the proteolytic activity of the serine protease;
(48)
a method for producing the peptide according to any one of (1) to (19) or the peptide derivative according to (20) inhibiting the proteolytic activity of a serine protease other than trypsin and/or acrosin, comprising the following steps (i) to (iii):
(i) contacting test peptides according to any one of (1) to (19) or test peptide derivatives according to (20) with the serine protease;
(ii) determining that the peptide or the peptide derivative is positive for inhibition, when the peptide or the peptide derivative inhibits the proteolytic activity of the serine protease; and
(iii) preparing, by gene recombination or in vitro translation, a peptide inhibiting the proteolytic activity, wherein said peptide corresponds to the peptide or in contained in the peptide derivative determined to be positive in step (ii);
(49)
a peptide selected from the following (i) and (ii):
(i) a peptide which comprises the amino acid sequence represented by SEQ ID NO: 1 in the Sequence Listing and satisfies the following (i1) to (i4):
(i1) each of the 1st Xaa to the 5th Xaa, the 7th Xaa, the 9th Xaa, and the 10th Xaa counting from the amino terminus of SEQ ID NO: 1 in the Sequence Listing is any amino acid other than cysteine and proline;
(i2) each of the 6th Xaa and the 8th Xaa counting from the amino terminus of SEQ ID NO: 1 in the Sequence Listing is any amino acid other than cysteine;
(i3) the 11th Xaa counting from the amino terminus of SEQ ID NO: 1 in the Sequence Listing is an amino acid selected from the group consisting of tyrosine, serine, phenylalanine, leucine, and threonine; and
(i4) the 12th Xaa counting from the amino terminus of SEQ ID NO: 1 in the Sequence Listing is an amino acid selected from the group consisting of asparagine, aspartic acid, leucine, lysine, glutamine, alanine, and glutamic acid; and
(ii) a peptide comprising an amino acid sequence derived from the amino acid sequence represented by SEQ ID NO: 1 in the Sequence Listing, in which conservative amino acid substitution, deletion, addition and/or insertion of 1 to 5 (inclusive) amino acids has occurred, wherein said substitution, deletion, addition and/or insertion has occurred at amino acids other than the 1st Xaa to the 12th Xaa counting from the amino terminus;
(50)
the peptide according to (49), wherein the conservative amino acid substitution occurs within any group selected from a hydrophobic amino acid group, a neutral hydrophilic amino acid group, an acidic amino acid group, a basic amino acid group, a group of amino acids influencing the direction of the main chain, and an aromatic amino acid group;
(51)
the peptide according to (49) or (50), wherein the peptide satisfies the following (i1) to (i12):
(i1) the 1st Xaa counting from the amino terminus of SEQ ID NO: 1 in the Sequence Listing is an amino acid selected from the group consisting of arginine, methionine, leucine, tryptophan, and serine;
(i2) the 2nd Xaa counting from the amino terminus of SEQ ID NO: 1 in the Sequence Listing is an amino acid selected from the group consisting of threonine, arginine, tryptophan, and phenylalanine;
(i3) the 3rd Xaa counting from the amino terminus of SEQ ID NO: 1 in the Sequence Listing is an amino acid selected from the group consisting of arginine, histidine, tryptophan, serine, and phenylalanine;
(i4) the 4th Xaa counting from the amino terminus of SEQ ID NO: 1 in the Sequence Listing is an amino acid selected from the group consisting of tryptophan, arginine, and leucine;
(i5) the 5th Xaa counting from the amino terminus of SEQ ID NO: 1 in the Sequence Listing is an amino acid selected from the group consisting of glycine, arginine, leucine, histidine, tryptophan, methionine, and tyrosine;
(i6) the 6th Xaa counting from the amino terminus of SEQ ID NO: 1 in the Sequence Listing is an amino acid selected from the group consisting of asparagine, histidine, proline, lysine, tryptophan, arginine, and aspartic acid;
(i7) the 7th Xaa counting from the amino terminus of SEQ ID NO: 1 in the Sequence Listing is an amino acid selected from the group consisting of arginine, phenylalanine, tryptophan, leucine, alanine, and glycine;
(i8) the 8th Xaa counting from the amino terminus of SEQ ID NO: 1 in the Sequence Listing is an amino acid selected from the group consisting of threonine, proline, asparagine, and serine;
(i9) the 9th Xaa counting from the amino terminus of SEQ ID NO: 1 in the Sequence Listing is an amino acid selected from the group consisting of tryptophan, methionine, tyrosine, and phenylalanine;
(i10) the 10th Xaa counting from the amino terminus of SEQ ID NO: 1 in the Sequence Listing is an amino acid selected from the group consisting of glutamine, valine, lysine, methionine, alanine, leucine, and asparagine;
(i11) the 11th Xaa counting from the amino terminus of SEQ ID NO: 1 in the Sequence Listing is an amino acid selected from the group consisting of tyrosine, phenylalanine, and leucine; and
(i12) the 12th Xaa counting from the amino terminus of SEQ ID NO: 1 in the Sequence Listing is lysine;
(52)
a derivative of a peptide according to any one of (49) to (51), the derivative being prepared by chemically modifying and/or biologically modifying the peptide;
(53)
the peptide according to any one of (49) to (51) or the peptide derivative according to (52) that binds to a predetermined target molecule; and
(54)
the peptide or the peptide derivative according to (53), wherein the target molecule is not an endogenous target of SPINK2; etc. for example but is not limited thereto.

Advantageous Effects of Invention

The present invention provides a peptide library useful in screening for a peptide binding to a desired target molecule.

BRIEF DESCRIPTION OF DRAWINGS

FIG. 1 is a diagram showing that SPINK2 mutants (polyclonal) were confirmed by ELISA to bind to a target molecule α-chymotrypsin, wherein the SPINK2 mutants obtained by panning against the target molecule were displayed on a phage. BSA was used as a negative control molecule.

FIG. 2 is a diagram showing that SPINK2 mutants (polyclonal) were confirmed by ELISA to bind to a target molecule plasma kallikrein, wherein the SPINK2 mutants obtained by panning against the target molecule were displayed on a phage. BSA was used as a negative control molecule.

FIG. 3 is a diagram showing that SPINK2 mutants (polyclonal) were confirmed by ELISA to bind to a target molecule hEGFR/Fc, wherein the SPINK2 mutants obtained by panning against the target molecule were displayed on a phage. BSA was used as a negative control molecule.

FIG. 4 is a diagram showing that SPINK2 mutants (polyclonal) were confirmed by ELISA to bind to a target molecule hHER2/Fc, wherein the SPINK2 mutants obtained by panning against the target molecule were displayed on a phage. BSA was used as a negative control molecule.

FIG. 5 is a diagram showing SDS-PAGE analysis under reducing conditions to analyze the molecular state of an α-chymotrypsin-binding peptide (single clone) expressed in *Escherichia coli* and then purified.

FIG. 6 is a diagram showing SDS-PAGE analysis under non-reducing conditions to analyze the molecular state of an α-chymotrypsin-binding peptide (single clone) expressed in *Escherichia coli* and then purified.

FIG. 7 is a diagram showing results of a quantitative ELISA assay for the binding affinities of 8 types of α-chymotrypsin-binding peptides expressed in *Escherichia coli* and then purified.

FIG. 8 is a diagram showing results of a quantitative ELISA assay for the binding affinities of α-chymotrypsin-binding peptide Nos. 2 and 6 (clones 2 and 6) expressed in *Escherichia coli* and then purified.

FIG. 9 is a diagram showing results of confirming, by ELISA, the target specificity of α-chymotrypsin-binding peptide No. 2 (clone 2) expressed in *Escherichia coli* and then purified.

FIG. 10 is a diagram showing results of confirming, by ELISA, the target specificity of α-chymotrypsin-binding peptide No. 6 (clone 6) expressed in *Escherichia coli* and then purified.

FIG. 11 is a diagram showing results of a quantitative assay for the chymotrypsin inhibitory activity of α-chymotrypsin-binding peptide Nos. 2 and 6 (clones 2 and 6) expressed in *Escherichia coli* and then purified.

FIG. 12 shows the amino acid sequences of random regions in 8 types of SPINK2 mutants (α-chymotrypsin-binding peptide Nos. 1, 2, 6, 7, 12 to 14, and 17) (SEQ ID NOs: 2 to 9).

FIG. 13 shows the amino acid sequence of a random region in a peptide having diversity (SEQ ID NO: 1). Amino acid positions 2 to 8 and 10 to 14 each represent any amino acid.

FIG. 14 shows the nucleotide sequence of fragment 1 (SEQ ID NO: 10).

FIG. 15-1 shows the nucleotide sequence of pCANTAB 5E (which will continue to FIG. 15-2).

FIG. 15-2 shows the nucleotide sequence of pCANTAB 5E (which will continue to FIG. 15-3; the nucleotide sequence of "fragment 2" is underlined and is SEQ ID NO: 11; which will continue to FIG. 15-3).

FIG. 15-3 shows the nucleotide sequence of pCANTAB 5E (which will continue to FIG. 15-4).

FIG. 15-4 shows the nucleotide sequence of pCANTAB 5E.

FIG. 16 shows the nucleotide sequence of fragment 3 (SEQ ID NO: 12).

FIG. 17 shows the nucleotide sequence of fragment 5 (SEQ ID NO: 13).

FIG. 18 shows a nucleotide sequence encoding the amino acid sequence of SPINK2 (SEQ ID NO: 14).

FIG. 19 shows an amino acid sequence encoded by the nucleotide sequence described in FIG. 18 (SEQ ID NO: 15).

FIG. 20-1 shows the nucleotide sequence of a template DNA for PCR comprising fragments 1 to 5 (SEQ ID NO: 16; which will continue to FIG. 20-2).

FIG. 20-2 shows the nucleotide sequence of a template DNA for PCR comprising fragments 1 to 5 (SEQ ID NO: 16: a sequel to FIG. 20-1).

DESCRIPTION OF EMBODIMENTS

The present invention provides a peptide, a derivative of the peptide, a peptide library, a nucleic acid, a vector, a cell, a method for producing the peptide and/or the derivative thereof, a method for identifying a peptide and/or a derivative thereof having desired properties, a method for producing a peptide and/or derivative thereof having desired properties, a method for determining whether or not a test peptide or test derivative thereof binds to a target molecule, a nucleic acid library, a composition, a reagent, etc. Hereinafter, various aspects of the present invention will be described. However, the aspects of the present invention are not limited thereto.

1. Peptide

The present invention provides a peptide.

The "peptide" of the present invention even incorporates a "polypeptide" and a "protein" in its meaning. In the present invention, this "peptide" even incorporates a "peptide derivative" in its meaning.

According to one aspect of the present invention, the peptide includes the amino acid sequence represented by SEQ ID NO: 1 in the Sequence Listing. In the amino acid sequence represented by SEQ ID NO: 1 included in the peptide, each of the 1st Xaa to the 12th Xaa counting from the amino terminus is any amino acid, preferably any amino acid other than cysteine.

According to a more preferred aspect of the present invention, in the amino acid sequence represented by SEQ ID NO: 1 in the Sequence Listing contained in the amino acid sequence of the peptide of the present invention, each of the 1st Xaa to the 5th Xaa, the 7th Xaa, the 9th Xaa, and the 10th Xaa counting from the amino terminus (corresponding to amino acids at positions 2 to 6, 8, 11, and 12, respectively, in SEQ ID NO: 1) is any amino acid other than cysteine and proline; each of the 6th Xaa and the 8th Xaa counting from the amino terminus (amino acids at positions 7 and 10, respectively, in SEQ ID NO: 1) is any amino acid other than cysteine; the 11th Xaa counting from the amino terminus (corresponding to an amino acid at position 13 in SEQ ID NO: 1) is an amino acid selected from the group consisting of tyrosine, serine, phenylalanine, leucine, and threonine; and the 12th Xaa counting from the amino terminus (corresponding to an amino acid at position 14 in SEQ ID NO: 1) is an amino acid selected from the group consisting of asparagine, aspartic acid, leucine, lysine, glutamine, alanine, and glutamic acid. Alternatively, each of the 1st Xaa to the 12th Xaa counting from the amino terminus may be an amino acid varied by conservative amino acid substitution (which is described in detail in the other part of the present invention) from an amino acid selected from each group described in this paragraph.

According to an even more preferred aspect of the present invention, in the amino acid sequence represented by SEQ ID NO: 1 in the Sequence Listing contained in the amino acid sequence of the peptide of the present invention, the 1st Xaa counting from the amino terminus (corresponding to an amino acid at position 2 in SEQ ID NO: 1) is an amino acid selected from the group consisting of arginine, methionine, leucine, tryptophan, and serine; the 2nd Xaa counting from the amino terminus (corresponding to an amino acid at position 3 in SEQ ID NO: 1) is an amino acid selected from the group consisting of threonine, arginine, tryptophan, and phenylalanine; the 3rd Xaa counting from the amino terminus (corresponding to an amino acid at position 4 in SEQ ID NO: 1) is an amino acid selected from the group consisting of arginine, histidine, tryptophan, serine, and phenylalanine; the 4th Xaa counting from the amino terminus (corresponding to an amino acid at position 5 in SEQ ID NO: 1) is an amino acid selected from the group consisting of tryptophan, arginine, and leucine; the 5th Xaa counting from the amino terminus (corresponding to an amino acid at position 6 in SEQ ID NO: 1) is an amino acid selected from the group consisting of glycine, arginine, leucine, histidine, tryptophan, methionine, and tyrosine; the 6th Xaa counting from the amino terminus (corresponding to an amino acid at position 7 in SEQ ID NO: 1) is an amino acid selected from the group consisting of asparagine, histidine, proline, lysine, tryptophan, arginine, and aspartic acid; the 7th Xaa counting from the amino terminus (corresponding to an amino acid at position 8 in SEQ ID NO: 1) is an amino acid selected from the group consisting of arginine, phenylalanine, tryptophan, leucine, alanine, and glycine; the 8th Xaa counting from the amino terminus (corresponding to an amino acid at position 10 in SEQ ID NO: 1) is an amino acid selected from the group consisting of threonine, proline, asparagine, and serine; the 9th Xaa counting from the amino terminus (corresponding to an amino acid at position 11 in SEQ ID NO: 1) is an amino acid selected from the group consisting of tryptophan, methionine, tyrosine, and phenylalanine; the 10th Xaa counting from the amino terminus (corresponding to an amino acid at position 12 in SEQ ID NO: 1) is an amino acid selected from the group consisting of glutamine, valine, lysine, methionine, alanine, leucine, and asparagine; the 11th Xaa counting from the amino terminus (corresponding to an amino acid at position 13 in SEQ ID NO: 1) is an amino acid selected from the group consisting of tyrosine, phenylalanine, and leucine; and the 12th Xaa counting from the amino terminus (corresponding to an amino acid at position 14 in SEQ ID NO: 1) is lysine. Alternatively, each of the 1st Xaa to the 12th Xaa counting from the amino terminus may be an amino acid varied by conservative amino acid substitution (which is described in detail in the other part of the present invention) from an amino acid selected from each group described in this paragraph.

According to a preferred aspect of the present invention, the peptide of the present invention may comprise, in addition to the amino acid sequence represented by SEQ ID NO: 1 in the Sequence Listing, an amino acid sequence encoded by a nucleotide sequence from the 1st base guanine or the 4th base cytosine to the 42nd base thymine in SEQ ID NO: 14 in the Sequence Listing either directly or via 1 or 2 or more arbitrary amino acids at the amino terminus of the amino acid sequence, or an amino acid sequence encoded by a nucleotide sequence from the 94th base guanine to the 189th base cytosine in SEQ ID NO: 14 in the Sequence Listing either directly or via 1 or 2 or more arbitrary amino acids at the carboxyl terminus thereof. The amino acid sequence of this peptide does not have to comprise aspartic acid encoded by the 1st base guanine to the 3rd base thymine in SEQ ID NO: 14 in the Sequence Listing, at its corresponding position. The amino acid sequence of this peptide may further comprise any additional amino acid sequence. Examples of such a peptide can include, but are not limited to, a peptide contained in a randomly mutated SPINK2 library prepared in Example 1 described later, and a peptide with a determined amino acid sequence of a random region screened for from the library in Example 3.

According to an aspect of the present invention, amino acid(s) except at the 1st Xaa to the 12th Xaa counting from the amino terminus in the amino acid sequence represented by SEQ ID NO: 1 in the Sequence Listing contained in the amino acid sequence of the peptide may be varied by substitution, deletion, addition, and/or insertion. In this amino acid sequence, the number of substituted, deleted, added, or inserted amino acid(s), except at the 1st Xaa to the 12th Xaa counting from the amino terminus of the amino acid sequence represented by SEQ ID NO: 1 in the Sequence Listing or the amino acid sequence corresponding to the sequence, can be 1 to 10 (inclusive). The lower limit thereof is 1. The upper limit thereof is 10, 9, 8, 7, 6, 5, 4, 3, or 2. 1 is the minimum limit thereof. The amino acid substitution is preferably conservative amino acid substitution.

In this amino acid sequence, each of the 1st Xaa to the 12th Xaa counting from the amino terminus of the amino acid sequence represented by SEQ ID NO: 1 in the Sequence Listing or the amino acid sequence corresponding to the sequence is any amino acid, preferably any amino acid other than cysteine, more preferably an amino acid selected from each group described above or an amino acid varied from the amino acid by conservative amino acid substitution.

A "conservative amino acid substitution" means the substitution of a certain amino acid by an amino acid functionally equivalent or similar thereto. The conservative amino acid substitution in the peptide brings about static change to the amino acid sequence of the peptide. For example, one or more amino acids similar in polarity to amino acid(s) in the peptide act functionally equivalently thereto and bring about static change to the amino acid sequence of this peptide. In general, substitution within a certain group can be regarded as being conservative in terms of structure and function. As is obvious to those skilled in the art, however, the role of a particular amino acid residue may have an implication on the three-dimensional structure of a molecule containing the amino acid. For example, a cysteine residue can take an oxidized (disulfide) form having lower polarity than that of a reduced (thiol) form. A long aliphatic moiety in an arginine side chain can constitute structurally and functionally important features. Also, an aromatic ring-containing side chain (tryptophan, tyrosine, and phenylalanine) can contribute to ion-aromatic interactions or cation-pi interactions. In this case, the substitution of an amino acid having such a side chain by an amino acid belonging to an acidic or nonpolar group can be structurally and functionally conservative. Residues such as proline, glycine, and cysteine (disulfide form) may have a direct impact on the three-dimensional structure of the main chain and can rarely be substituted without structural distortion.

A conservative amino acid substitution includes, as shown below, specific substitution based on side chain similarity (L. Lehninger, Biochemistry, 2nd edition, pp 73-75, Worth Publisher, New York (1975)) and typical substitution.

(1) Nonpolar amino acid group: alanine (hereinafter, referred to as "Ala" or simply as "A"), valine (hereinafter, referred to as "Val" or simply as "V"), leucine (hereinafter, referred to as "Leu" or simply as "L"), isoleucine (hereinafter, referred to as "Ile" or simply as "I"), proline (hereinafter, referred to as "Pro" or simply as "P"), phenylalanine (hereinafter, referred to as "Phe" or simply as "F"), tryptophan (hereinafter, referred to as "Trp" or simply as "W"), and methionine (hereinafter, referred to as "Met" or simply as "M")

(2) Uncharged polar amino acid group: glycine (hereinafter, referred to as "Gly" or simply as "G"), serine (hereinafter, referred to as "Ser" or simply as "S"), threonine (hereinafter, referred to as "Thr" or simply as "T"), cysteine (hereinafter, referred to as "Cys" or simply as "C"), tyrosine (hereinafter, referred to as "Tyr" or simply as "Y"), asparagine (hereinafter, referred to as "Asn" or simply as "N"), and glutamine (hereinafter, referred to as "Gln" or simply as "Q")
(3) Acidic amino acid group: aspartic acid (hereinafter, referred to as "Asp" or simply as "D") and glutamic acid (hereinafter, referred to as "Glu" or simply as "E")
(4) Basic amino acid group: lysine (hereinafter, referred to as "Lys" or simply as "K"), arginine (hereinafter, referred to as "Arg" or simply as "R"), and histidine (hereinafter, referred to as "His" or simply as "H")

Naturally occurring amino acids can be divided into the following groups based on the properties of their common side chains:
(1) Hydrophobic amino acid group: norleucine, Met, Ala, Val, Leu, and Ile
(2) Neutral hydrophilic amino acid group: Cys, Ser, Thr, Asn, and Gln
(3) Acidic amino acid group: Asp and Glu
(4) Basic amino acid group: His, Lys, and Arg
(5) Group of amino acids influencing the direction of the main chain: Gly and Pro
(6) Aromatic amino acid group: Trp, Tyr, and Phe.

Hereinafter, examples of the conservative substitution will be shown. However, the conservative amino acid substitution of the present invention is not limited thereto.

Ala may be substituted by, for example, Val, Leu, Ile, Met, norleucine, Pro, Phe, or Trp.

Arg may be substituted by, for example, Lys or His.

Asn may be substituted by, for example, Cys, Ser, Thr, Gln, Tyr, or Gly.

Asp may be substituted by, for example, Glu.

Cys may be substituted by, for example, Gly, Ser, Thr, Tyr, Asn, or Gln.

Gln may be substituted by, for example, Gly, Ser, Thr, Cys, Tyr, or Asn.

Glu may be substituted by, for example, Asp.

Gly may be substituted by, for example, Ser, Cys, Thr, Tyr, Asn, Gln, Pro, Asp, or Glu.

His may be substituted by, for example, Lys or Arg.

Ile may be substituted by, for example, Leu, Val, Met, Pro, Ala, Phe, Trp, or norleucine.

Leu may be substituted by, for example, norleucine, Ile, Val, Pro, Met, Ala, Phe, Trp, or Met.

Lys may be substituted by, for example, Arg or His.

Met may be substituted by, for example, Ala, Val, Leu, Phe, Ile, Pro, Trp, or norleucine.

Norleucine may be substituted by, for example, Met, Ala, Val, Leu, Ile, Pro, Phe, or Trp.

Phe may be substituted by, for example, Trp, Leu, Val, Ile, Ala, Tyr, Pro, or Met.

Pro may be substituted by, for example, Ala, Val, Leu, Ile, Phe, Trp, Met, or Gly.

Ser may be substituted by, for example, Thr, Cys, Asn, Gln, Gly, or Tyr.

Thr may be substituted by, for example, Val, Ser, Gly, Cys, Tyr, Asn, or Gln.

Trp may be substituted by, for example, Tyr, Phe, Ala, Val, Leu, Ile, Pro, or Met.

Tyr may be substituted by, for example, Gly, Cys, Asn, Gln, Trp, Phe, Thr, or Ser.

Val may be substituted by, for example, Ile, Leu, Met, Trp, Phe, Ala, norleucine, or Pro.

Examples of the amino acid sequence (corresponding to the amino acid sequence represented by SEQ ID NO: 1 in the Sequence Listing: random region) contained in the amino acid sequence of the peptide of the present invention having the amino acid sequence constituted of these amino acids can include the following, though the amino acid sequence of the peptide of the present invention is not limited thereto:

CRTRW GNRCT WQYKP VC (SEQ ID NO: 2 in the Sequence Listing: α-chymotrypsin-binding peptide No. 1 shown in FIG. 12)

CMRHR RHFCT MVYKP VC (SEQ ID NO: 3 in the Sequence Listing: α-chymotrypsin-binding peptide No. 2 shown in FIG. 12)

CRRWL LPWCT YKYKP VC (SEQ ID NO: 4 in the Sequence Listing: α-chymotrypsin-binding peptide No. 6 shown in FIG. 12)

CLWRR HKLCP FKFKP VC (SEQ ID NO: 5 in the Sequence Listing: α-chymotrypsin-binding peptide No. 7 shown in FIG. 12)

CWRSW RWACP YMYKP VC (SEQ ID NO: 6 in the Sequence Listing: α-chymotrypsin-binding peptide No. 12 shown in FIG. 12)

CWFFR WRWCN WALKP VC (SEQ ID NO: 7 in the Sequence Listing: α-chymotrypsin-binding peptide No. 13 shown in FIG. 12)

CSTWR MWGCP WLYKP VC (SEQ ID NO: 8 in the Sequence Listing: α-chymotrypsin-binding peptide No. 14 shown in FIG. 12)

CWRRW YDRCS FNLKP VC (SEQ ID NO: 9 in the Sequence Listing: α-chymotrypsin-binding peptide No. 17 shown in FIG. 12)

In the present invention, the amino acid can be L-amino acid, D-amino acid, or a mixture thereof (DL-amino acid) but means L-amino acid unless otherwise specified.

In the present invention, an amino acid may be any of amino acids other than those described above (hereinafter, these amino acids are collectively referred to as "abnormal amino acids" for the sake of convenience). Examples of abnormal amino acids can include selenocysteine, N-formylmethionine, pyrrolysine, pyroglutamic acid, cystine, hydroxyproline, hydroxylysine, thyroxine, O-phosphoserine, desmosine, β-alanine, sarcosine, ornithine, creatine, γ-aminobutyric acid, opine, theanine, tricholomic acid, kainic acid, domoic acid, and acromelic acid, which are found in natural peptides or proteins. Examples of non-natural amino acids can include, but not limited to: N-terminally protected amino acids such as Ac-amino acid, Boc-amino acid, Fmoc-amino acid, Trt-amino acid, and Z-amino acid; C-terminally protected amino acids such as t-butyl ester, benzyl ester, cyclohexyl ester, and fluorenyl ester of amino acids; and other amino acids including diamine, ω amino acid, β amino acid, γ amino acid, Tic derivatives of amino acids, and aminophosphonic acid.

The peptide of the present invention can be prepared by a method for producing peptides or proteins well known to those skilled in the art, such as chemical synthesis, gene recombination, or in vitro translation. Also, the peptide identified or screened for from the library of the present invention or the like can be prepared by such a method.

Examples of the chemical synthesis method can include, but are not limited to, a t-butoxycarbonyl (Boc) method and a 9-fluorenylmethoxycarbonyl (Fmoc) method. The Fmoc method has advantages such as mild deprotection conditions and the convenient excision of peptides from resins (Fmoc solid phase peptide synthesis: a practical approach, ed. by W. C. Chan, P. D. White Eds., Oxford University Press, New York, 2000.).

In the present invention, the "derivative of the peptide" and the "peptide derivative" mean a chemically modified or biologically modified form of the peptide of the present invention. The chemical modification means the conversion of the original peptide into a different substance through a chemical reaction, i.e., the formation or cleavage of an atom-atom bond, in or on the peptide of the present invention. The biological modification means the conversion of the original peptide into a different substance through a biological reaction, i.e., through the use of an organism-derived protein (enzyme, cytokine, etc.), nucleic acid (ribozyme, etc.), cell, tissue, or organ, or a non-human individual or by the direct or indirect action thereof, in or on the peptide of the present invention.

This "derivative" is not particularly limited as long as the derivative is a substance different from the original peptide. Examples thereof can include a substance containing a naturally occurring sugar chain or an artificially developed sugar chain, a substance containing a polymer such as polyethylene glycol (PEG), a substance containing a synthetic compound or a natural compound, a labeled substance, a substance containing a moiety necessary for solid-phase immobilization, a substance containing a signal peptide linked to the amino terminus, a substance containing a tag for use in purification or isolation, a substance containing an amino acid or an amino acid sequence derived from a vector suitable for display, panning, expression, etc., a substance containing an amino acid or an amino acid sequence produced by the variation of a nucleotide sequence encoding the peptide in order to circumvent frame shift or to introduce restriction enzyme sites, and a substance in which a peptide as a phenotype is linked directly or indirectly to a genotype corresponding to the phenotype, and combinations of two or more thereof.

The derivative of the peptide of the present invention can be prepared by subjecting the peptide of the present invention, as a starting material, to a method for chemically or biologically modifying peptides or proteins that is well known to those skilled in the art, such as chemical reaction, biochemical reaction, or post-translational modification. The derivative of the peptide identified or screened for from the library of the present invention or the like can also be prepared by such a method. Alternatively, the post-translationally modified peptide derivative of the present invention may be prepared by gene recombination using a cell capable of providing desired post-translational modification. In addition, the peptide derivative of the present invention containing a modified amino acid can be prepared by adding the modified amino acid to an in vitro translation system.

Examples of the PEGylation method can include, but are not limited to, a method involving reacting peptides or proteins with N-hydroxysuccinimide ester (NHS)-PEG.

According to a preferred aspect, the peptide of the present invention and the derivative thereof each bind to a target molecule (which is described in detail in the other part of the present invention). The peptide of the present invention that binds to a predetermined target molecule is useful as, for example, a reagent for testing various diseases for which the target molecule can serve as a marker. As mentioned above, the present invention encompasses a peptide having an amino acid sequence derived from the amino acid sequence represented by SEQ ID NO: 1 in the Sequence Listing contained in the amino acid sequence of the peptide by the substitution, deletion, addition, and/or insertion of 1 to several (the term "several" means any integer of 1 to 10) amino acids except at the 1st Xaa to the 12th Xaa counting from the amino terminus. According to a preferred aspect, this peptide binds to a target molecule. Preferably, the target molecule is a predetermined one.

Examples of the form that can be taken by the peptide of the present invention and the derivative thereof can include, but are not limited to, an isolated form (freeze-dried preparation, solution, etc.), a form bound with an additional molecule (solid-phase immobilized form, fusion protein, an assembly with a foreign molecule, form bound with a target molecule, etc.), a physical collection containing even other peptides, etc. (including the peptide library of the present invention), a form expressed or displayed on cell surface (on *Escherichia coli* or yeast cell surface, etc.) (including the cell of the present invention), and a form expressed or displayed on a viral particle. A form suitable for a purpose such as use or storage can be selected freely.

2. Nucleic Acid

The present invention provides a nucleic acid.

In the present invention, the "nucleotide" is a mononucleotide, an oligonucleotide, or a polynucleotide and is also referred to as a "nucleic acid", a "nucleic acid molecule" or a "gene". Examples of the nucleic acid of the present invention can include, but not limited to, DNA, cDNA, RNA, mRNA, cRNA, probes, oligonucleotides, polynucleotides, primers, and vectors. Also, the nucleic acid of the present invention can be any of single-stranded nucleotides, double-stranded nucleotides, and an hybrid of 3 or more nucleotide strands and encompasses even a single-stranded nucleotides hybrid consisting of DNA and RNA, a double-stranded nucleotides consisting of the nucleotide and its complementary strand, a double-stranded hybrid consisting of single-stranded DNA and single-stranded RNA, double-stranded RNA, single-stranded nucleotides that may have a double-stranded structure moiety in its molecule, etc. The nucleic acid of the present invention may further contain one or more (artificially developed) bases or one or more mononucleotides, other than naturally occurring bases or mononucleotides.

Preferred examples of the nucleic acid of the present invention can include a nucleic acid comprising nucleotides consisting of a nucleotide sequence encoding the amino acid sequence of the peptide of the present invention, and a nucleic acid comprising a nucleotide sequence encoding the amino acid sequence of the peptide of the present invention. This preferred nucleic acid may contain a nucleotide sequence other than the nucleotide sequence encoding the amino acid sequence of the peptide of the present invention, and/or a non-nucleotide moiety and may be modified chemically or biologically (which is described in the other part of the present invention). These forms are all encompassed by the "nucleic acid".

The nucleic acid of the present invention also encompasses a nucleic acid consisting of a nucleotide sequence encoding the amino acid sequence of the peptide of the present invention.

In the present invention, in the case where the amino acid sequence of the peptide of the present invention is encoded by a portion or the whole of the nucleotide sequence of certain nucleotides, this nucleic acid is referred to as a "nucleic acid corresponding to the peptide" and this peptide is referred to as a "peptide corresponding to the nucleic acid".

Examples of the nucleic acid corresponding to the peptide of the present invention can include, but are not limited to, a nucleic acid comprising a nucleic acid consisting of a nucleotide sequence encoding the amino acid sequence of the peptide of the present invention, a nucleic acid comprising a nucleotide sequence encoding the amino acid sequence of the peptide of the present invention, and a nucleic acid consisting of a nucleotide sequence encoding the amino acid sequence of the peptide of the present invention.

Examples of the peptide corresponding to the nucleic acid of the present invention can include, but are not limited to, a peptide comprising a peptide consisting of an amino acid sequence encoded by a portion or the whole of the nucleotide sequence of the nucleic acid of the present invention, a peptide comprising an amino acid sequence encoded by a portion or the whole of the nucleotide sequence of the nucleic acid of the present invention, a peptide consisting of an amino acid sequence encoded by a portion or the whole of the nucleotide sequence of the nucleic acid of the present invention, and a derivative of any one of these peptides.

In the present invention, the phrase "genotype corresponding to (the) phenotype" is also used interchangeably with the "nucleic acid corresponding to the peptide". Likewise, the phrase "phenotype corresponding to (the) genotype" is also used interchangeably with the "peptide corresponding to the nucleic acid".

When the chemically or biologically modified form of the nucleic acid of the present invention contains the peptide of the present invention, this modified form is encompassed in the scope of the "derivative of the peptide" of the present invention.

More preferred examples of the nucleic acid of the present invention can include, of the preferred nucleic acid described above, a nucleic acid comprising a nucleic acid consisting of a nucleotide sequence encoding the amino acid sequence of the peptide of the present invention that binds to a target molecule, a nucleic acid comprising a nucleotide sequence encoding the amino acid sequence of the peptide of the present invention that binds to a target molecule, and a nucleic acid consisting of a nucleotide sequence encoding the amino acid sequence of the peptide of the present invention that binds to a target molecule.

In the present invention, one or more codons corresponding to each amino acid can be used for designing the nucleotide sequence encoding the amino acid sequence. Hence, a nucleotide sequence encoding the single amino acid sequence of a certain peptide or protein may have a plurality of variations. For the selection of such codons, the codons can be selected appropriately according to the codon usage of cells (host cells) to harbor a genotype corresponding to the peptide, i.e., a nucleic acid comprising the nucleotide sequence encoding the peptide, or the frequency or rate of a plurality of codons used can be adjusted appropriately. For example, in the case of using *Escherichia coli* cells as host cells, the nucleotide sequence can be designed using codons with high frequency of use in *Escherichia coli*.

The nucleic acid of the present invention can be prepared by a method for producing a nucleic acid well known to those skilled in the art, such as chemical synthesis or gene recombination. A nucleic acid encoding the amino acid sequence of the peptide recovered from the library of the present invention or the like (including screened for, enriched, and isolated) by the identification method of the present invention can also be prepared by such a method.

Examples of the form that can be taken by the nucleic acid of the present invention can include, but are not limited to, an isolated form (freeze-dried preparation, solution, etc.), a form bound with an additional molecule (solid-phase immobilized form, etc.), a recombinant vector comprising the nucleic acid (the vector of the present invention), a cell in which the nucleic acid or the vector (the cell of the present invention) is introduced, a form contained in a virus or a viral particle (including a form contained as the vector of the present invention), and a physical collection containing even other nucleic acids, etc. (including the nucleic acid library of the present invention). A form suitable for a purpose such as use or storage can be selected freely.

3. Vector

The present invention provides a recombinant vector (hereinafter, also simply referred to as a "vector").

The vector of the present invention is not particularly limited as long as the vector comprises the nucleic acid of the present invention and serves as means for transferring the nucleic acid of the present invention to cells, microorganisms, or individuals. Preferred examples thereof can include nucleic acid vectors such as phagemids, cosmids, and plasmids.

The vector of the present invention may be a virus that infects prokaryotic cells or eukaryotic cells, or a viral vector.

In the present invention, the "phagemid" means a bacterial plasmid containing an origin of plasmid replication as well as the second replication origin derived from a single-stranded bacteriophage. A cell having this phagemid can replicate the phagemid via a single strand replication mode in coinfection with M13 or its analogous helper bacteriophage. Specifically, single-stranded phagemid DNA is packaged in an infective particle coated with a bacteriophage coat protein. In this way, the phagemid DNA can be formed as a cloned double-stranded DNA plasmid in the infected bacterium, while the phagemid can be formed as a bacteriophage-like particle from the culture supernatant of the coinfected cell. In order to infect a bacterium having F-pilus with the DNA, the bacteriophage-like particle can be injected into the bacterium to reform the particle itself as a plasmid.

A fusion gene comprising the nucleic acid corresponding to the peptide of the present invention and a bacteriophage coat protein gene can be inserted to the phagemid. Bacterial cells can be infected with the resulting phagemid and cultured to express or present (a synonymous with display) the peptide on the bacterium or a phage-like particle or to produce a fusion protein of the peptide and the coat protein into a phage particle or the culture supernatant of the bacterium.

For example, a fusion gene comprising the nucleic acid corresponding to the peptide of the present invention and a bacteriophage coat protein gene gpIII can be inserted to the phagemid. *Escherichia coli* can be coinfected with the resulting phagemid and M13 or its analogous helper phage to produce a fusion protein comprising the peptide and the coat protein into the culture supernatant of the *Escherichia coli*. This fusion protein is encompassed in the scope of the peptide derivative of the present invention.

Instead of the phagemid, various circular or noncircular vectors, preferably viral vectors, may be used to express or present (a synonymous with display) the peptide encoded by the nucleotide sequence of the nucleic acid of the present invention contained in the vector, on a cell or a virus-like particle in which the vector is introduced, or to produce the peptide into the culture supernatant of the cell according to a method well known to those skilled in the art.

The vector (recombinant vector) of the present invention can be prepared by a method well known to those skilled in the art such as gene recombination.

Examples of the form that can be taken by the vector of the present invention can include, but are not limited to, an isolated form (freeze-dried preparation, solution, etc.), a form bound with an additional molecule (solid-phase immobilized form, etc.), a form transferred to a cell (including the recombinant cell of the present invention), and a physical collection containing even other vectors, etc. (including a particular aspect of the nucleic acid library of the present invention). A form suitable for a purpose such as use or storage can be selected freely.

4. Cell

According to one aspect, the present invention provides a recombinant cell (hereinafter, also simply referred to as a "cell").

The cell of the present invention is a cell that contains a nucleic acid corresponding to the peptide of the present invention and that expresses the peptide. Any of eukaryotic cells (including established cell lines, primary cultured cells, and subcultured cells) and prokaryotic cells can be used as a host cell or cell of the present invention without particular limitations.

Examples of the prokaryotic cells can include, but are not limited to, bacterial cells such as *Escherichia coli* and *Bacillus subtilis* cells.

Examples of the eukaryotic cells can include animal cells, insect cells, yeast cells, and fungal cells. Examples of the animal cells can include, but are not limited to, monkey COS cells (Gluzman, Y., Cell (1981), vol. 23, pp 175-182; American Type Culture Collection No. ATCC CRL-1650), mouse fibroblasts NIH3T3 (American Type Culture Collection No. ATCC CRL-1658), Chinese hamster ovary cells (CHO cells; American Type Culture Collection No. ATCC CCL-61), and dihydrofolate reductase-deficient lines of CHO cells (Urlaub, G. and Chasin, L. A., Proc. Natl. Acad. Sci. USA (1980), vol. 77, pp 4126-4220).

The cell of the present invention can be prepared by transferring the nucleic acid of the present invention or the vector of the present invention to a host cell and can be prepared preferably by transferring the vector of the present invention to a host cell by transfection, transformation, transduction, or the like.

Examples of the vector suitable for the preparation of the cell of the present invention can include, but are not limited to, replicons derived from a species compatible with the prokaryotic cell, i.e., plasmids, cosmids, and phagemids containing a replication origin and one or more nucleotide sequences selected from a regulatory sequence, transcription initiation site, start codon and stop codon (of translation), etc. The nucleic acid or the vector may further contain a nucleotide sequence that can confer phenotypic character (phenotype) selectivity to the cell in which the vector or the nucleic acid is introduced. Such a vector or nucleic acid can be transferred to a host cell, and the obtained cell can be cultured to express the peptide of the present invention.

A host cell suitable for the post-translational modification of the peptide of the present invention may be used as the cell of the present invention. The cell of the present invention can be used in (an aspect of) the method for preparing the peptide derivative of the present invention, for example.

Examples of the form that can be taken by the cell of the present invention can include, but are not limited to, an isolated form (frozen preparation, freeze-dried preparation, solution, etc.), a form bound with an additional molecule (solid-phase immobilized form, etc.), a cell in which the nucleic acid or the vector of the present invention (which is included in the cell of the present invention) is introduced, a cell expressing or presenting (a synonymous with displaying) the peptide of the present invention on its surface (which is included in the cell of the present invention), and a physical collection containing even other cells, etc. (including a particular aspect of the nucleic acid library and the peptide library of the present invention). A form suitable for a purpose such as use or storage can be selected freely.

5. Method for Producing Peptide

According to an alternative aspect, the present invention also provides a method for producing the peptide of the present invention.

The peptide of the present invention can be prepared, as mentioned above, by a method for producing peptides or proteins well known to those skilled in the art, such as chemical synthesis, gene recombination, or in vitro translation. A peptide recovered from the library of the present invention or the like (including screened for, enriched, and isolated) by the identification method of the present invention can also be prepared by such a method.

According to an aspect of the present invention, the method for producing the peptide of the present invention comprises the following steps (1-1) and (1-2):

(1-1) culturing a cell (the cell of the present invention) that contains the nucleic acid corresponding to the peptide of the present invention and that expresses the peptide or the like; and (1-2) recovering the peptide from the culture.

According to an alternative aspect, the method for producing the peptide of the present invention comprises the following steps (2-1) and (2-2):

(2-1) determining the amino acid sequence of the peptide of the present invention that binds to a target molecule; and (2-2) preparing a peptide consisting of the amino acid sequence by chemical synthesis or gene recombination.

According to a further alternative aspect, the method for producing the peptide of the present invention comprises the following steps (3-1) and (3-2):

(3-1) preparing mRNA corresponding to the peptide of the present invention; and (3-2) preparing the peptide by in vitro translation with the mRNA obtained in step (3-1) as a template.

Also, each of these production methods can be combined appropriately with the identification method of the present invention as a previous step. Specifically, first, steps included in the identification method of the present invention are carried out, and subsequently, steps included in the production method of the present invention can be carried out. The method for producing the peptide of the present invention may encompass such a method further comprising (each step of) the identification method of the present invention.

Such a method for producing the peptide of the present invention comprises, for example, the following steps (4-1) to (4-3):

(4-1) contacting peptides contained in the peptide library of the present invention with a target molecule;

(4-2) recovering a peptide that binds to the target molecule; and (4-3) preparing the recovered peptide by chemical synthesis, gene recombination, or in vitro translation.

Likewise, each of these production methods can be combined appropriately with the determination method of the present invention as a previous step. Specifically, first, steps included in the determination method of the present invention are carried out, and subsequently, steps included in the production method of the present invention can be carried out. The method for producing the peptide of the present invention or the like may encompass such a method further comprising (each step of) the determination method of the present invention.

Such a method for producing the peptide of the present invention or the like comprises, for example, the following steps (5-1) to (5-3):
(5-1) contacting test peptides of the present invention with a target molecule;
(5-2) determining that the test peptide is positive for binding when the test peptide binds to the target molecule, and
(5-3) when the test peptide has been determined to be positive in step (5-2), preparing the peptide by chemical synthesis, gene recombination, or in vitro translation.

According to an alternative aspect, the method for producing the peptide of the present invention further comprises the step of identifying a peptide that binds to a target molecule other than trypsin and/or acrosin which are endogenous target molecules of SPINK2, preferably other than trypsin, and, partially or completely, activates or promotes, or, inhibits, inactivates or suppresses, the biological activity of the target molecule. This production method comprises, for example, the following steps (6-1) to (6-3) or (7-1) to (7-3):
(6-1) contacting peptides contained in the peptide library of the present invention with the target molecule;
(6-2) recovering a peptide that binds to the target molecule; and
(6-3) determining that the peptide is positive, when the peptide activates or promotes the biological activity of the target molecule or agonizes the target molecule, or
(7-1) contacting peptides contained in the peptide library of the present invention with the target molecule;
(7-2) recovering a peptide that binds to the target molecule; and
(7-3) determining that the peptide is positive, when the peptide inhibits, inactivates, or suppresses the biological activity of the target molecule or antagonizes the target molecule.

According to a further alternative aspect, the production method of the present invention comprises, for example, the following steps (8-1) and (8-2) or (9-1) and (9-2) instead of the steps (6-1) to (6-3) or (7-1) to (7-3):
(8-1) contacting test peptides with a target molecule other than trypsin and/or acrosin, preferably other than trypsin; and
(8-2) determining that the peptide is positive, when the peptide activates or promotes the biological activity of the target molecule, or agonizes the target molecule, or
(9-1) contacting test peptides with a target molecule other than trypsin and/or acrosin, preferably other than trypsin; and
(9-2) determining that the peptide is positive, when the peptide inhibits, inactivates, or suppresses the biological activity of the target molecule, or antagonizes the target molecule.

The peptide that activates or promotes the biological activity of the target molecule or the peptide that agonizes the target molecule (agonistic peptide) can be produced by the steps (6-1) to (6-3) or (8-1) and (8-2), or the like combined with a step equivalent to the step (4-3) or (5-3), or the like. Likewise, the peptide that inhibits, inactivates, or suppresses the biological activity of the target molecule or the peptide that antagonizes the target molecule (antagonistic peptide) can be produced by the steps (7-1) to (7-3) or (9-1) and (9-2), or the like combined with a step equivalent to the step (4-3) or (5-3), or the like.

The present invention also provides a method for producing the derivative of the peptide (peptide derivative) of the present invention. The peptide derivative of the present invention can be prepared, for example, by the method described above (method for producing the peptide) and then subjecting the prepared peptide to chemical reaction, biochemical reaction, post-translational modification, or the like, but not limited thereto.

Instead of the peptide prepared in the step (2-2), (3-2), (4-3), or (5-3), a peptide (X') having an amino acid sequence derived from the amino acid sequence of the peptide (X) by the deletion of 1 or 2 or more amino acids or partial amino acid sequences may be prepared. The present invention also encompasses a method for producing the peptide (X'). The peptide (X') prepared by this method preferably binds to a target molecule. In the amino acid sequence of such a preferred peptide (X'), 1 or 2 or more amino acids or partial amino acid sequences that are contained in the amino acid sequence of the original peptide, but are not essential for binding to the target molecule may be deleted.

Examples of the method for producing the peptide derivative of the present invention can include, but are not limited to, a method comprising each of the steps (1-1) and (1-2), (2-1) and (2-2), (3-1) and (3-2), (4-1) to (4-3), (5-1) to (5-3), (6-1) to (6-3), (7-1) to (7-3), (8-1) and (8-2), or (9-1) and (9-2), or the like and further comprising the step of preparing the peptide derivative of the present invention using the peptide of the present invention as a starting material (hereinafter, referred to as a "derivative preparation step"), a method comprising the step of preparing the peptide derivative instead of the peptide in each of the steps (2-2), (3-2), (4-3), and (5-3), a method using a peptide library originally containing the peptide derivative, and a method using test peptide derivatives instead of the test peptides.

Instead of the peptide derivative prepared in the step (2-2), (3-2), (4-3), or (5-3) that may be comprised in the method for producing the peptide derivative of the present invention, a peptide derivative (Y') having an amino acid sequence derived from the amino acid sequence of the peptide derivative (Y) by the deletion of 1 or 2 or more amino acids or partial amino acid sequences may be prepared. The present invention also encompasses a method for producing the peptide derivative (Y'). The peptide derivative (Y') prepared by this method preferably binds to a target molecule. In the amino acid sequence of such a preferred peptide derivative (Y'), 1 or 2 or more amino acids or partial amino acid sequences that are contained in the amino acid sequence of the original peptide derivative, but are not essential for binding to the target molecule may be deleted. Alternatively, a cell capable of providing desired post-translational modification may be used in the method for producing the peptide of the present invention to prepare the peptide derivative of the present invention as a peptide provided with the desired post-translational modification. In this case, for example, the cell capable of providing desired post-translational modification can be used as the cell in the steps (1-1) and (1-2) or as a cell (or host cell) applied to the gene recombination in the steps (2-2), (4-3) and (5-3) to prepare the peptide derivative provided with the desired post-translational modification, though the method for preparing the post-translationally modified form of the peptide (as an aspect of the method for producing the peptide derivative) of the present invention is not limited thereto.

6. Library

The present invention provides a library.

In the present invention, the "library" means a physical collection of molecules that are analogous, but not identical, to one another. The molecules contained in this collection can coexist, for example, in one container or may be present in a physically isolated manner as groups or individual molecules in different containers or at different sites on a solid-phase support. A plurality of libraries may be contained in one collection.

The library of the present invention is not limited by any means as long as the library is a physical collection containing non-identical peptides and/or nucleic acids of the present invention. Examples thereof can include a phage display library, a ribosome display library, and a nucleic acid display library.

The "phage display" means a technique (method and means therefor) of linking foreign peptides or proteins to the coat proteins of filamentous phages or the like and expressing or displaying the resulting fusion proteins on phage-like particles. Also, the recovery (including screening, enrichment, and isolation) of nucleic acids corresponding to the peptides or proteins using this technique is encompassed in the scope of the "phage display". The phage display library is one aspect of the library of the present invention used in this technique.

The "ribosome display" means a technique (method and means therefor) of expressing or displaying peptides or proteins in the form of complexes comprising three molecules (mRNA-ribosome-peptide or protein), which are formed during the translation reaction of in vitro translation. In this context, the peptides or proteins are translation products of the mRNAs. Also, the recovery (including screening, enrichment, and isolation) of nucleic acids corresponding to the peptides or proteins using this technique is encompassed in the scope of the "ribosome display". The ribosome display library is an alternative aspect of the library of the present invention used in this technique.

The "nucleic acid display" means a technique (method and means therefor) of expressing or displaying peptides or proteins in the form of complexes comprising a nucleic acid (synonymous with nucleic acids) and peptides or proteins corresponding to the nucleic acid (Keefe, A. D and Szostak, J. W., Nature, vol. 410 (2001), pp 715-718). Also, the recovery (including screening, enrichment, and isolation) of a nucleic acid corresponding to the peptides or proteins using this technique is encompassed in the scope of the "nucleic acid display". The nucleic acid display library is a further alternative aspect of the library of the present invention used in this technique.

Examples of the nucleic acid display can include, but not limited to, mRNA display (Yamaguchi, J. et al., Nucleic Acids Research, vol. 37, No. 16 e108, pp 1-13 (2009)).

The mRNA display is a technique of displaying peptides or proteins in the form of complexes comprising mRNAs and their translation products peptides or proteins associated via intervening moieties (Keefe, A. D and Szostak, J. W., Nature, vol. 410 (2001), pp 715-718).

In the present invention, a physical collection of cells, a physical collection of microorganisms (including viruses, phages, phage-like molecules, particles thereof, etc.), and a physical collection of naturally occurring or artificially developed vectors (including phagemids, cosmids, plasmids, etc.), which comprise a physical collection containing non-identical peptides and/or nucleic acids of the present invention, as well as a physical collection of fragments thereof and a physical collection of chemically and/or biologically modified forms thereof are also encompassed in the scope of the "library".

In the present invention, as mentioned above, one or more codons corresponding to each amino acid can be used for designing the nucleotide sequence encoding the amino acid sequence. Hence, a nucleotide sequence encoding the single amino acid sequence of a certain peptide or protein may have a plurality of variations. For the selection of such codons, the appropriate codons can be selected according to the codon usage of cells (host cells) in which a genotype corresponding to the peptide, i.e., a nucleic acid comprising the nucleotide sequence encoding the peptide, is introduced, or the frequency or rate of a plurality of codons used can be adjusted appropriately. Accordingly, in the nucleic acid library of the present invention, each nucleic acid comprising a nucleotide sequence encoding the single amino acid sequence may have a plurality of variations. Specifically, the nucleic acid library of the present invention may comprise a physical collection containing nucleic acids, each comprising a nucleotide sequence encoding the amino acid sequence of a certain peptide. This physical collection of the nucleic acids corresponding to the particular peptide may form in itself one nucleotide library.

The library of the present invention contains a plurality of molecules that are analogous, but not identical, to one another. The (number of) types of analogous molecules contained in the library are referred to as the "diversity of (the) library". For example, the diversity of a library consisting of 100 types of analogous molecules is $10^2$. In the present invention, the diversity of the library is not particularly limited and preferably has a higher value.

The diversity of the peptide library for use in the identification method of the present invention and the method for producing the peptide, comprising the steps of the identification method is $1 \times 10^5$ or higher, $2 \times 10^5$ or higher, $5 \times 10^5$ or higher, $1 \times 10^6$ or higher, $2 \times 10^6$ or higher, $5 \times 10^6$ or higher, $1 \times 10^7$ or higher, $2 \times 10^7$ or higher, $5 \times 10^7$ or higher, $1 \times 10^8$ or higher, $2 \times 10^8$ or higher, $5 \times 10^8$ or higher, $1 \times 10^9$ or higher, $2 \times 10^9$ or higher, $5 \times 10^9$ or higher, $1 \times 10^{10}$ or higher, $2 \times 10^{10}$ or higher, $5 \times 10^{10}$ or higher, $1 \times 10^{11}$ or higher, $2 \times 10^{11}$ or higher, $5 \times 10^{11}$ or higher, $1 \times 10^{12}$ or higher, $2 \times 10^{12}$ or higher, $5 \times 10^{12}$ or higher, $1 \times 10^{13}$ or higher, $2 \times 10^{13}$ or higher, $5 \times 10^{13}$ or higher, $1 \times 10^{14}$ or higher, $2 \times 10^{14}$ or higher, $5 \times 10^{14}$ or higher, $1 \times 10^{15}$ or higher, $2 \times 10^{15}$ or higher, $5 \times 10^{15}$ or higher, $1 \times 10^{16}$ or higher, $2 \times 10^{16}$ or higher, $5 \times 10^{16}$ or higher, or $1 \times 10^{17}$ or higher. Such diversity of the library is not limited to an actual measured value and may be a theoretical value.

7. Identification Method

The present invention provides a method for identifying a peptide and/or a peptide derivative binding to a target molecule. The identification method of the present invention may comprise, for example, the steps (4-1) and (4-2), (6-1) and (6-2), (7-1) and (7-2), or the like, though the identification method of the present invention is not limited thereto.

(1) Target Molecule

In the present invention, the "target molecule" means a substance to which the peptide of the present invention binds and also means an endogenous substance present in a human or nonhuman animal individual or an exogenous substance incorporated in vivo into the individual. The target molecule of the present invention is preferably a molecule other than trypsin and/or acrosin which are endogenous targets of SPINK2, more preferably other than trypsin. The target molecule of the present invention is even more preferably a human-derived molecule other than human-derived trypsin. The target molecule of the present invention is still even more preferably any of endogenous or exogenous enzymes, receptors, ligands of the receptors, humoral factors (e.g., cytokines), other biopolymers, signal transducers, cells, pathogens, toxins, and substances derived from any one or more thereof, for example, fragments, decomposition products, metabolites, or processed products thereof, which can be involved in directly or indirectly in the onset or exacerbation of a disease that may affect the human individual, or exhibits correlation or inverse correlation with the disease (hereinafter referred to as "disease-related target molecule"). Alternatively, the target molecule of the present invention may be any of non-natural substances such as minerals, polymers, plastics, and synthetic low-molecular-weight compounds.

According to an aspect of the present invention, the target molecule is preferably a protease other than trypsin and/or acrosin, more preferably other than trypsin. The target molecule is even more preferably a serine protease, further preferably an endo-type serine protease. Examples of the endo-type serine protease can include chymotrypsin. For the purification and/or isolation of a particular protein component from a tissue, a body fluid, a cell, etc., a suitable protease inhibitor can be added to a fraction containing this component to thereby reduce the lysis of the component. Such a protease inhibitor is useful in the production of various recombinant and non-recombinant proteins.

Also, the protease is preferably a disease-related target molecule.

The target molecule of the present invention is used, for example, for screening the peptide library of the present invention for a peptide that binds to the target molecule, a peptide that agonizes the target molecule, or a peptide that antagonizes the target molecule, or for determining the binding activity, agonistic activity, or antagonistic activity of a test peptide against the target molecule. The target molecule may be a full-length molecule or a fragment thereof, or a derivative thereof, with any amino acid, peptide, protein, sugar chain, polymer, carrier, or the like added thereto. Alternatively, the target molecule may be solid-phase immobilized.

(2) Preparation of Target Molecule

The target molecule of the present invention can be isolated and/or purified, for use, from a tissue or a cell affected with a disease or can be used in the form in which the whole or a portion thereof is bound to or contained in the tissue, the cell, or the like. Also, the target molecule of the present invention can be prepared by a method for producing peptides or proteins that is well known to those skilled in the art, such as chemical synthesis, gene recombination, or in vitro translation. From the target molecule thus obtained, the derivative as mentioned above may be prepared, if necessary.

In the present invention, the target peptide or protein can be prepared by, for example: in vitro translation, i.e., a method involving incubating a nucleic acid (such as DNA or cDNA) corresponding to this peptide or protein or a vector containing the nucleic acid in a solution containing an enzyme, a substrate, an energetic material, etc., necessary for transcription and translation to synthesize the desired peptide or protein in vitro; gene recombination, i.e., a method involving transferring the nucleic acid or the vector to prokaryotic or eukaryotic cells (host cells), culturing the obtained recombinant cells, and then recovering the desired peptide or protein from the culture; or chemical synthesis.

In the case where the target molecule is a protein present or a domain thereof on a cell membrane, the molecule can also be prepared as a secreted protein by expressing, in an appropriate host-vector system, a fusion protein comprising the extracellular region of this protein or domain linked to an immunoglobulin (Ig) constant region.

The nucleic acid corresponding to the target molecule can be obtained by, for example, an expression cloning method, though the obtainment method is not limited thereto. The expression cloning method involves constructing an expression library of cDNAs comprising nucleotide sequences encoding the amino acid sequences of peptides or proteins, and performing polymerase chain reaction (hereinafter, referred to as "PCR"; Saiki, R. K., et al., Science (1988), vol. 239, pp 487-489) with this cDNA library as a template using primers specifically amplifying the full length or partial length of the cDNAs to clone cDNAs corresponding to the peptides or proteins.

Examples of kits or reagents applicable to the in vitro translation can include Rapid Translation System (RTS) manufactured by Roche Diagnostics K.K.

Prokaryotic or eukaryotic cells applicable as host cells for preparing the cell of the present invention can be selected appropriately as the host cells for gene recombination.

The recombinant cell (cell in which the nucleic acid or the vector is introduced) obtained by gene recombination can be cultured according to a method well known to those skilled in the art and can be allowed to produce the desired peptide or protein into the culture or into the cell.

The medium for use in this culture can be selected appropriately from among those routinely used according to the host cells. In the case of using *Escherichia coli* cells as host cells, for example, an LB medium can be supplemented, if necessary, with an antibiotic (e.g., ampicillin) and IPTG and subjected to the culture.

The desired peptide or protein produced intracellularly or extracellularly from the recombinant cell by this culture can be purified and isolated by the appropriate combination of fractionation approaches known in the art using, for example, its physical, chemical, and/or biological properties.

Examples of the fractionation approaches can include, but are not limited to, salting out, treatment with a protein precipitant, dialysis, ultrafiltration, molecular sieve (gel filtration) chromatography, adsorption chromatography, ion-exchange chromatography, affinity chromatography, partition chromatography, and hydrophobic chromatography.

Alternatively, a moiety useful for purification may be linked or added to the peptide or protein in advance. As a result, the desired peptide or protein can be purified efficiently. For example, a histidine tag consisting of 6 residues can be linked to the peptide or protein in advance to efficiently purify the desired peptide or protein by nickel affinity chromatography. Alternatively, an IgG Fc region can be liked thereto in advance to efficiently purify the desired peptide or protein by protein A affinity chromatography.

(3) Contact of Peptide and/or Peptide Derivative with Target Molecule

The identification method of the present invention comprises the step of contacting peptides and/or derivatives thereof with the target molecule. In this context, the peptides and/or the derivatives thereof may be contained in the peptide library. Specifically, the identification method of the present invention may comprise the step of contacting peptides and/or derivatives thereof contained in the peptide library with the target molecule.

In the present invention, the term "contacting" means that two or more substances are brought into proximity so that two or more of these substances can interact with each other. Examples of the interaction can include, but are not limited to: covalent bonds, coordinate bonds, metal-metal bonds, ionic bonds, metallic bonds, hydrogen bonds, and Van der Waals bond (hereinafter, these bonds are referred to as "chemical bonds"); interactions based on electrostatic interactions such as bonds based on Coulomb force, interionic interactions, hydrogen bonds, dipolar interactions, and Van der Waals force (hereinafter, these interactions are referred to as "intermolecular force"); and other interactions, chargetransfer interactions, transannular interactions, hydrophobic interactions, and association of peptides and biomolecules. In the present invention, the "two or more substances" are not particularly limited as long as the substances include the target molecule and a test substance. The test substance is not particularly limited as long as the substance binds to the target molecule. Examples thereof can include the peptide of the present invention, the derivative of the peptide, a solid-phase carrier with the peptide or the peptide derivative immobilized thereon, and a cell, a viral particle, or a virus-like particle (including phages and phagemids) expressing or displaying the peptide or the peptide derivative. The test substance may be expressed or displayed on the surface of a eukaryotic or prokaryotic cell, on a viral particle or a virus-like particle, or in a ribosome- or nucleic acid-linked form by phage display, ribosome display, nucleic acid display, or the like.

(4) Screening

The identification method of the present invention comprises the step of screening for a peptide and/or a peptide derivative having desired properties, preferably a peptide and/or a peptide derivative binding to the target molecule.

In the present invention, the terms "binding" or "bound" means that two or more substances are in proximity or in an associated state with each other under a certain condition to the extent that these substances can interact (which is described in the other part of the present invention) with each other.

In the present invention, test substances are contacted with target molecules under a certain condition. Subsequently, a test substance nonspecifically adsorbed to the target molecule and a test substance unbound or unadsorbed to the target molecule is removed from a test substance-containing fraction. If a test substance is present in the resulting fraction, this test substance can be regarded as "binding" to the target molecule.

When mere nonspecific adsorption occurs between two or more substances, the "binding" can be regarded as not occurring between these substances. In addition, when two or more substances contacted with each other are neither in proximity nor in an associated state with each other to the extent that these substances can interact (which is described in the other part of the present invention) with each other, the "binding" can be regarded as not occurring between the substances.

For example, a fluorescence antibody method (direct or indirect method), radioimmunoassay, enzyme immunoassay (homogeneous or heterogeneous method), ELISA, or ELISPOT, which performs assay by flow cytometry or the like is widely used as a method for determining the "binding" between an antibody and an antigen. In these methods, the presence or absence of the "binding" between the peptide or the derivative thereof and the target molecule can be determined in the same way as in the determination of the "binding" between an antibody and an antigen except that the test antibody and the antigen are replaced with the peptide of the present invention or the derivative thereof and the target molecule.

Also, the presence or absence of the "binding" can be determined by measuring an index for binding activity or affinity. Examples of the index for binding affinity can include a dissociation constant and an association constant.

Provided that the chemical equilibrium between a molecule A and an A-binding substance B is defined as follows:

 [Formula 1]

the dissociation constant (Kd) of chemical dissociation thereof can be calculated according to the following expression:

$$Kd=[A][B]/[AB]$$

wherein [A], [B], and [AB] represent the concentrations of the molecule A, the substance B, and an assembly AB, respectively; Kd represents the ratio of the molecule A and the substance B dissociated from each other to the undissociated assembly AB; and the reciprocal of Kd represents an association constant (Ka).

The "dissociation constant" used in the present invention means mainly the equilibrium dissociation constant of the peptide and/or the peptide derivative for binding to a certain target molecule.

In the present invention, the dissociation constant can be calculated by measuring the concentrations of dissociated substances (peptide, peptide derivative, target molecule, etc.) and undissociated substances (assembly of the peptide and/or the peptide derivative and the target molecule, etc.). The method for determining and calculating the dissociation constant is not particularly limited as long as the method is well known to those skilled in the art. Examples thereof can include a method using surface plasmon resonance and an isothermal titration calorimetry method.

In the method using surface plasmon resonance, the interaction between the target molecule and the peptide and/or the derivative thereof binding thereto can be determined and calculated as follows: a series of association and dissociation reactions is detected by surface plasmon resonance at a plurality of peptide concentrations; the obtained series of association and dissociation reactions is analyzed; and the dissociation constant is calculated from various rate constants thus obtained.

Examples of the determination-calculation system of surface plasmon resonance can include, but not limited to, Biacore system (GE Healthcare Japan Corp.). Procedures for the method using Biacore system are as follows: target molecules are immobilized onto a sensor chip of Biacore system by amine coupling; the target molecules are contacted with peptides at a plurality of peptide concentrations; the interaction therebetween is detected by surface plasmon resonance; a series of association and dissociation reactions is drawn in a sensorgram with time as the abscissa against the amount of binding (RU) as the ordinate; the sensorgram drawn at the plurality of peptide concentrations is fit to a 1:1 Langmuir model using BIAevaluation software (manufactured by GE Healthcare Japan Corp.) to calculate various rate parameters; and the dissociation constant is calculated from various rate parameters thus calculated.

In the isothermal titration calorimetry method, the interaction between the target molecule and the peptide and/or the derivative thereof binding thereto can be determined and calculated as follows: a peptide solution is added dropwise to a target molecule-containing solution (or vice versa); the quantity of heat generated by the interaction is measured to draw a binding isotherm; and a dissociation constant (KD), stoichiometry of the reaction (N), an enthalpy change (ΔH), and an entropy change (ΔS) are obtained from the binding isotherm.

Examples of the system of directly measuring a very small thermal change (exothermic change or endothermic change) associated with an intermolecular interaction can include, but are not limited to, MicroCal system (GE Healthcare Japan Corp.). Procedures for the method using MicroCal system are as follows: a ligand solution is titrated to each sample cell kept at constant temperature, and stirred; heat generation or absorption directly proportional to the amount of binding take place through the intermolecular interaction to change the temperature of the solution in the sample cell; a temperature difference ($\Delta T$) from a reference cell is detected by a cell feedback network (CFB); the reference cell or the sample cell is heated until $\Delta T$ reaches 0; a feedback power required to maintain $\Delta T=0$ is measured to obtain the quantity of heat generated or absorbed through the interaction; the amount of heat generated is plotted as an ordinate against the molar ratio of the peptide to the target molecule as an abscissa, and the dissociation constant is calculated from the binding isotherm.

In the identification method and/or the determination method (which will be described later) of the present invention, a test substance that exhibits a dissociation constant of, for example, 100 µM or smaller, 50 µM or smaller, 20 µM or smaller, 10 µM or smaller, 5 µM or smaller, 2 µM or smaller, 1 µM or smaller, 500 nM (0.5 µM) or smaller, 200 nM or smaller, 100 nM or smaller, 50 nM or smaller, 20 nM or smaller, 10 nM or smaller, 5 nM or smaller, 2 nM or smaller, 1 nM or smaller, 500 pM (0.5 nM) or smaller, 200 pM or smaller, 100 pM or smaller, 50 pM or smaller, 20 pM or smaller, 10 pM or smaller, 5 pM or smaller, 2 pM or smaller, or 1 pM or smaller for the target molecule can be determined to bind to the target molecule, i.e., to be positive, though the reference value of the dissociation constant and the criteria for determining the presence or absence of the "binding" are not limited thereto.

In the identification method of the present invention, the "screening" step also serves as the step of recovering the test substance that binds to the target molecule. The product may consist only of the test substance binding to the target molecule or may also contain a substance that does not bind to the target molecule as long as the test substance binding to the target molecule is contained or enriched in the product. The target molecule-binding test substance contained or enriched in this product may be a single substance or may be a mixture of two or more of such substances.

The screening step, i.e., the recovery step, in the identification method of the present invention means the step of recovering a fraction having the target molecule-binding substance contained or enriched therein. This step is not particularly limited as long as the step is performed by a fractionation-purification method well known to those skilled in the technical field of the present invention. The step may comprise, for example, the steps of: separating a substance bound with the target molecule, a substance unbound with the target molecule and a substance nonspecifically adsorbed to the target molecule from the (fraction containing) target molecule; or eluting the substance bound with the target molecule (separating the substance from the target molecule). In this step, the criteria for determining the dissociation constant or the like do not have to be set for the presence or absence of binding.

In the present invention, the "screening" included in the identification method of the present invention is also referred to as "panning". In the present invention, the "panning" means procedures of contacting peptides and/or peptide derivatives of the present invention with a target molecule and recovering (including screening for, concentrating, and isolating) a peptide and/or a peptide derivative binding to the target molecule.

A method well known to those skilled in the art can be applied to the panning. Examples thereof can include, but not limited to, a solid-phase panning method and a liquid-phase panning method. The solid-phase panning method can involve, for example, immobilizing target molecules onto a solid phase, subsequently contacting peptides contained in a liquid phase with the target molecules, subsequently removing a peptide unbound with the target molecule and a nonspecifically bound peptide, and then selectively separating a peptide bound with the target molecule from (the target molecule immobilized on) the solid phase to screen for a peptide having the desired binding activity, though the operation of the solid-phase panning method is not limited thereto. The liquid-phase panning method can involve, for example, contacting peptides with the target molecules in a solution, subsequently removing a peptide unbound with the target molecule and a nonspecifically bound peptide, and then selectively separating a peptide bound with the target molecule from the target to screen for a peptide having the desired binding activity, though the operation of the liquid-phase panning method is not limited thereto.

In the identification method of the present invention, the nucleic acid corresponding to the peptide (including even the "peptide derivative") binding to the target molecule are efficiently screened for using a library in which a phenotype (synonymous with a phenotypic character) is linked to a genotype (synonymous with a genetic character) corresponding thereto. As a result, the peptide can be prepared efficiently. The link between the phenotype and the genotype corresponding thereto (hereinafter, simply referred to as a "phenotype and a genotype") may be direct or indirect.

The "direct link" between the phenotype and the genotype means that the behaviors of the phenotype and the genotype match with each other. Even if there is a degree of distance between the phenotype and the genotype, for example, due to the presence of an additional intervening moiety, this case is also encompassed in the scope of the "direct link" as long as their behaviors match with each other. Specifically, it is not essential that they should be physically adjacent to each other.

In the present invention, the phrase "behaviors of the phenotype and the genotype match with each other" means that their behaviors match with each other in aspects such as the peptide, the nucleic acid, the vector, the cell, the production method, the identification method, the determination method, the peptide library, the nucleic acid library, the composition, and the reagent of the present invention. In these aspects, even if the "match of the behaviors" is lost wholly or partially due to an internal factor, an external factor, their combination, or any of other factors over time, for the time being, until a certain point in time, or from a certain point in time onward, this case is also encompassed in the scope of the phrase "behaviors match with each other".

Examples of the direct link between the phenotype and the genotype can include a ribosome display library, a nucleic acid display library, a peptide and/or a derivative thereof linked directly or indirectly to the nucleic acid corresponding to the peptide of the present invention, and a peptide library comprising this peptide and/or derivative thereof.

The "indirect link" between the phenotype and the genotype means that a particular phenotype allows access to a genotype corresponding to the phenotype, though their behaviors do not always match with each other or they are not necessarily "directly linked" to each other. Examples of the indirect link between the phenotype and the genotype can include, but are not limited to, a phage display library and cDNA library for use in expression cloning.

Even though the behavior of the peptide or the derivative thereof as a phenotype does not necessarily match with that of the nucleic acid as a genotype corresponding thereto, in each clone contained in the phage display library or the cDNA library, the peptide and/or the derivative thereof (expressed or displayed on a phage-like particle) binding to the target molecule can be screened for through the steps, for example, of contacting peptides and/or derivatives thereof contained in the library with the target molecule, removing a phage-like particle unbound with the target molecule or nonspecifically adsorbed to the target molecule, and then selectively eluting a phage-like particle bound with the target molecule. In addition, the corresponding genotype, i.e., the nucleic acid corresponding to this peptide or the peptide derivative thereof can be purified and isolated and further sequenced. The advantages of such access from the phenotype to the genotype corresponding thereto are not limited to the case of the "indirect link" between the phenotype and the genotype in the phage display, etc., and can also be appreciated in the case of the "direct link" therebetween.

Each step included in the identification method of the present invention can be performed repetitively two or more times. In particular, a new peptide library can be constructed from peptides and/or peptide derivatives recovered in the screening step, and then subjected to the contact and screening steps to enrich, at a higher level, the peptide and/or the derivative thereof binding to the target molecule. This operation can be further repeated to enrich, at a much higher level, the peptide and/or the derivative thereof binding to the target molecule. Finally, the efficiency of isolation thereof can be enhanced. In addition, this higher level of enrichment of the peptide and/or the derivative thereof binding to the target molecule achieves isolation of a binder having higher affinity.

Alternatively, the peptide and/or the derivative thereof binding to the target molecule may be enriched at a higher level by more securely separating the target-bound peptide and/or derivative thereof from a nonspecifically bound one in the step included in the identification method of the present invention. Examples of such a separation method include increase in the number of the step removing a nonspecifically bound peptide, etc., and the change of a reagent (surfactant, etc.) for use in the removal of the nonspecifically bound peptide to a stronger one.

The peptide of the present invention or the derivative thereof can take any form of a monomer, a homo- or hetero-dimer, a trimer, a tetramer, a pentamer, a hexamer, a heptamer, an octamer, and a multimer composed of 9 or more monomers.

The number of the molecule of the peptide of the present invention or the derivative thereof binding to one target molecule or one target site can be any of 1, 2, 3, 4, 5, 6, 7, 8, and 9 or more. This peptide or derivative thereof can bind to the target molecule, in any form of a monomer, a homo- or hetero-dimer, a trimer, a tetramer, a pentamer, a hexamer, a heptamer, an octamer, and a multimer composed of 9 or more monomers.

The number of the target molecule or the target site to which one molecule of the peptide of the present invention or the derivative thereof binds can be any of 1, 2, 3, 4, 5, 6, 7, 8, and 9 or more.

The present invention also provides a method for identifying a peptide or a peptide derivative that partially or completely activates or promotes or partially or completely inhibits, inactivates, or suppresses the biological activity of a target molecule, and a method for identifying a peptide or a peptide derivative that agonizes or antagonizes a target molecule. Specifically, the present invention provides a method for identifying an activator, a promoter, or an agonist of a target molecule or an inhibitor, an inactivator, a suppressor, or an antagonist of a target molecule. These identification methods may each comprise the steps (6-1) to (6-3), (7-1) to (7-3), or the like, though the identification methods are not limited to methods comprising these steps.

8. Composition

The present invention provides a composition.

The composition of the present invention comprises the peptide, the peptide derivative, the nucleic acid, the vector, or the cell of the present invention.

The composition comprising the peptide of the present invention or the derivative thereof (including those displayed on the surface of the cell of the present invention) can be used for detecting a target molecule to which the peptide or the derivative thereof binds.

The composition comprising the nucleic acid, the vector, or the cell of the present invention can be used for preparing a peptide having an amino acid sequence encoded by the nucleotide sequence of the nucleic acid, or the nucleic acid contained in the vector, or the cell of the present invention. Also, this composition can be used for detecting a nucleic acid, a vector, a cell, etc., containing the nucleic acid.

The composition can comprise, if necessary, for example, a buffer, a salt, a metal, an antiseptic, a surfactant, and a substance for reducing or preventing damage to the peptide, the peptide derivative, the nucleic acid, the vector, or the cell of the present invention by a preparation method such as freezing or freeze drying.

9. Reagent

The present invention provides a reagent.

The reagent of the present invention comprises the peptide, the peptide derivative, the nucleic acid, the vector, or the cell of the present invention.

The reagent comprising the peptide of the present invention or the derivative thereof can be used for detecting a target molecule to which the peptide or the derivative thereof binds.

For example, pancreatic enzymes such as elastase or trypsin are known to be synthesized by pancreatic acinar cells and secreted as a pancreatic juice into the pancreatic duct system. When pancreatic tissue damage occurs due to various inflammatory stimuli or the like, these enzymes are deviated in large amounts into blood. A rise in pancreatic enzyme level in blood can therefore be measured to thereby diagnose the presence or absence of pancreatic damage.

The reagent comprising the nucleic acid, the vector, or the cell of the present invention can be used for detecting a nucleic acid, a vector, a cell, etc., containing the nucleic acid.

The reagent of the present invention may be a composition.

A kit comprising the reagent is also encompassed by the reagent of the present invention.

Also, the peptide or the peptide derivative of the present invention, the cell displaying the peptide or the peptide derivative, etc., can be used as an element recognizing a substance such as a target molecule, in a biosensor for the substance.

10. Determination Method

The present invention provides even a method for determining whether or not a test substance binds to a target molecule. The determination method of the present invention may comprise, for example, the above-mentioned steps (5-1) and (5-2), though the determination method of the present invention is not limited thereto.

The determination method of the present invention can employ the same steps as in the steps included in the identification method of the present invention or steps appropriately modified from these steps. The test substance, however, which is subjected to this determination method, does not have to be contained in a collection such as a library. For example, a test peptide or a test peptide derivative subjected to the determination method is not limited to the peptide or the peptide derivative contained in the peptide library and may be a single peptide or peptide derivative separated from other peptides, a mixture containing them, or the like. Specifically, the identification method of the present invention is suitable mainly as a method for identifying one or more molecules having desired properties from the physical collection of test substances, whereas the determination method of the present invention is also suitable as an assay method for examining whether or not a particular test substance has desired properties.

In the determination method of the present invention, for example, determination in the step of determining whether or not the test substance binds to the target molecule can be performed on the basis of whether or not the test substance satisfies conditions regarding an index for affinity such as a dissociation constant. In the screening step, as in the identification method of the present invention, the test substance can be determined to be positive if the test substance is recovered as a substance binding to the target molecule.

The present invention also provides a method for determining whether or not the test substance partially or completely activates or promotes or partially or completely inhibits, inactivates, or suppresses the biological activity of a target molecule, and a method for determining whether or not the test substance agonizes a target molecule or antagonizes a target molecule. These determination methods of the present invention may each comprise the steps (8-1) and (8-2), (9-1) and (9-2), or the like, though the determination methods are not limited to methods comprising these steps.

EXAMPLES

Hereinafter, the present invention will be described specifically with reference to Examples. However, these Examples are not intended to limit the technical scope of the present invention by any means. Plasmids, restriction enzymes, DNA modification enzymes, and the like used in Examples of the present invention are commercially available and can be used according to routine methods. Operations used in DNA cloning, polynucleotide sequencing, transformation of host cells, culture of transformed cells, collection of enzymes from the resulting culture, purification, etc. are well known to those skilled in the art and can be easily known by literatures or the like.

Example 1

(1-1) Preparation of Randomly Mutated SPINK2 Library

Phagemid vectors were constructed in order to display a randomly mutated SPINK2 library on phages. First, a region containing a tTH terminator was synthesized to prepare "fragment 1 (SEQ ID NO: 10)". A region from nucleotide positions 2097 to 2232 (SEQ ID NO: 11) of pCANTAB 5E (GE Healthcare Japan Corp.) containing a lac operator was synthesized to prepare "fragment 2". A sequence (SEQ ID NO: 12) comprising an SD sequence and a phoA signal peptide was synthesized as "fragment 3". The pCANTAB 5E-derived sequence of a phage coat protein (gene III) was synthesized as "fragment 4". A region containing an Ipp terminator was synthesized as "fragment 5 (SEQ ID NO: 13)". The "fragment 1" to the "fragment 5" were used as templates for overlap extension PCR ((94° C. for 15 seconds, 60° C. for 30 seconds, and 68° C. for 160 seconds)×30 cycles) using the following primers 1 and 2 and KOD-plus- (Toyobo Co., Ltd.; which is composed of DNA polymerase, a buffer solution, a substrate, etc.):

```
Primer 1:
5'-AAAAAACGCGTCTGCGGCCGCATAGGGTAGCGAAAACCT-3'

Primer 2:
5'-AAAAAGGCGCCATTCGCCATTCAGGCTGCGCAACTGTTGG-3'
```

The amplified fragment was subjected to agarose gel electrophoresis. Then, the desired DNA fragment was excised and purified with Wizard SV Gel and PCR Clean-Up System (Promega KK.) to prepare DNA. The prepared DNA fragment and pCANTAB 5E were each treated with restriction enzymes AflIII (New England Biolabs Japan Inc.) and NarI (New England Biolabs Japan Inc.) at 37° C. for 1 hour or longer. After agarose gel electrophoresis, the desired DNA fragments were excised and purified with Wizard SV Gel and PCR Clean-Up System. The purified fragments were reacted overnight at 16° C. using T4 DNA Ligase (New England Biolabs Japan Inc.) to carry out ligation reaction. The ligation solution was added to *Escherichia coli* JM109 (Toyobo Co., Ltd.), and the mixture was left standing on ice for 30 minutes, then heat-treated at 42° C. for 45 seconds, and then further left standing on ice for 5 minutes. The *Escherichia coli* was seeded over a 2-YT plate containing 0.1 mg/ml ampicillin and then transformed by overnight static culture at 37° C. On the next day, the transformed *Escherichia coli* was inoculated to a Terrific Broth medium (Invitrogen Corp.) containing 0.1 mg/ml ampicillin and cultured overnight at 37° C. Then, plasmid DNA was recovered using QIAprep 96 Turbo Miniprep Kit (Qiagen N.V.) (hereinafter, this operation is referred to as "miniprep treatment"). The obtained DNA was sequenced to confirm that the vector of interest was constructed. This vector was designated as a "phagemid vector pPR3". The phagemid vector pPR3 can be used in Examples described in the paragraph (1-3) or later, instead of a phagemid vector pPR3_SPINK2(WT) constructed in the paragraph (1-2).

(1-2) Construction of Phagemid Vector pPR3_SPINK2(WT)

Phagemid vectors were constructed in order to display a randomly mutated SPINK2 library on phages. First, a region containing a tTH terminator was prepared as "fragment 1 (SEQ ID NO: 10)". A region from nucleotide positions 2099 to 2232 (corresponding to nucleotide positions 3 to 136 in SEQ ID NO: 11) of pCANTAB 5E (GE Healthcare Japan Corp.) containing a lac operator was prepared as "fragment 2". A sequence (SEQ ID NO: 12) comprising an SD sequence, a phoA signal peptide, and a nucleotide sequence encoding the amino acid sequence of wild-type SPINK2, i.e., SPINK2(WT) was prepared as "fragment 3". The pCANTAB 5E-derived sequence (from nucleotide positions 600 to 1848 in SEQ ID NO: 16) containing a phage coat protein (gene III) was synthesized as "fragment 4". A region containing an Ipp terminator was prepared as "fragment 5 (SEQ ID NO: 13)". A nucleotide sequence (SEQ ID NO: 16) comprising the "fragment 1" to the "fragment 5" was used as a template for overlap extension PCR ((94° C. for 15 seconds, 60° C. for 30 seconds, and 68° C. for 160 seconds)× 30 cycles) using the following primers 1 and 2 and KOD-plus- (Toyobo Co., Ltd.; which is composed of DNA polymerase, a buffer solution, a substrate, etc.):

Primer 1':
5'-AAAAGAAGAGCGCCCAATACGCAAACCGCCTCTCC-3'

Primer 2':
5'-AAAAAGAATTCATTAAACGGCAGACAAAAAAATGTCGC-3'

The amplified fragment was subjected to agarose gel electrophoresis. Then, the desired DNA fragment was excised and purified with Wizard SV Gel and PCR Clean-Up System (Promega KK.) to prepare DNA. The prepared DNA fragment and pCANTAB 5E were each treated with restriction enzymes SapI (New England Biolabs Japan Inc.) and EcoRI (New England Biolabs Japan Inc.) at 37° C. for 1 hour or longer. After agarose gel electrophoresis, the desired DNA fragments were excised and purified with Wizard SV Gel and PCR Clean-Up System. The purified fragments were reacted overnight at 16° C. using T4 DNA Ligase (New England Biolabs Japan Inc.) to carry out ligation reaction. The ligation solution was added to *Escherichia coli* JM109 (Toyobo Co., Ltd.), and the mixture was left standing on ice for 30 minutes, then heat-treated at 42° C. for 45 seconds, and then further left standing on ice for 5 minutes. The *Escherichia coli* was seeded over a 2-YT plate containing 0.1 mg/ml ampicillin and then transformed by overnight static culture at 37° C. On the next day, the transformed *Escherichia coli* was inoculated to a Terrific Broth medium (Invitrogen Corp.) containing 0.1 mg/ml ampicillin and cultured overnight at 37° C. Then, plasmid DNA was recovered using QIAprep 96 Turbo Miniprep Kit (Qiagen N.V.) (hereinafter, this operation is referred to as "miniprep treatment"). The obtained DNA was sequenced to confirm that the vector of interest was constructed. The constructed vector was further treated with a restriction enzyme EcoRI at 37° C. for 1 hour or longer. After Klenow treatment, ligation reaction was carried out at 16° C. for 1 hour using T4 DNA Ligase (New England Biolabs Japan Inc.). *Escherichia coli* JM109 was transformed with the ligation product. The transformed *Escherichia coli* was cultured and then subjected to miniprep treatment. The obtained DNA was sequenced, and the constructed vector was designated as a "phagemid vector pPR3_SPINK2(WT)" and used in the subsequent Examples.

(1-3) Construction of Phagemid Vector pPR3_stuffer_TEV

Next, a TEV protease cleavage sequence and a stuffer were inserted to the phagemid vector pPR3_SPINK2(WT). In order to prepare the TEV protease cleavage sequence, overlap extension PCR ((94° C. for 15 seconds, 60° C. for 30 seconds, and 68° C. for 10 seconds)×30 cycles) was performed using the following primers 3 and 4 and KOD-plus-:

Primer 3:
5'-GCGGCCGCATAGGGTAGCGAAAACCTGTATTTTCAGAG-3'

Primer 4:
5'-GCTAAACAACTTTCAACGGTgctaccGCTCTGAAAATACAGG-3'

The amplified fragment was subjected to agarose gel electrophoresis. Then, the desired DNA fragment was excised and purified with Wizard SV Gel and PCR Clean-Up System to prepare DNA as "fragment 6". The vector pPR3_SPINK2(WT) constructed in the paragraph (1-2) was used as a template for PCR ((94° C. for 15 seconds, 60° C. for 30 seconds, and 68° C. for 30 seconds)×30 cycles) using the following primers 5 and 6 and KOD-plus- to amplify the phage coat protein (gene III):

Primer 5: 5'-ACCGTTGAAAGTTGTTTAGCAAAACCC-3'

Primer 6: 5'-CATTAAAGCCAGAATGGAAAGCGCAGTC-3'

The amplified DNA fragment was further used as a template for PCR ((94° C. for 15 seconds, 60° C. for 30 seconds, and 68° C. for 45 seconds)×30 cycles) using the following primers α and β and KOD-plus-:

Primer α: 5'-AACACGCGTCTGCGGCCGCATAGGGTAGC-3'

Primer β: 5'-AACGGATCCTCATTAAAGCCAGAATGGAAAG-3'

The amplified fragment was subjected to agarose gel electrophoresis. Then, the desired DNA fragment was excised and purified with Wizard SV Gel and PCR Clean-Up System to prepare DNA. The prepared DNA fragment and pPR3_SPINK2(WT) constructed in the paragraph (1-2) were each treated with restriction enzymes MluI (New England Biolabs Japan Inc.) and BamHI (New England Biolabs Japan Inc.) at 37° C. for 1 hour or longer. After agarose gel electrophoresis, the desired DNA fragments were excised and purified with Wizard SV Gel and PCR Clean-Up System. The purified fragments were reacted overnight at 16° C. using T4 DNA Ligase to carry out ligation reaction. *Escherichia coli* JM109 was transformed with the ligation product. The transformed *Escherichia coli* was cultured and then subjected to miniprep treatment. The obtained DNA was sequenced. The constructed vector was designated as a "phagemid vector pPR3_TEV". The operation was performed according to the method described in the paragraph (1-1).

The constructed phagemid vector pPR3_TEV and pcDNA3.1(+) (Invitrogen Corp.) were each treated with restriction enzymes EcoRI (New England Biolabs Japan Inc.) and MluI (New England Biolabs Japan Inc.) at 37° C. for 1 hour or longer. After agarose gel electrophoresis, the desired DNA fragments were excised and purified with Wizard SV Gel and PCR Clean-Up System. The purified fragments were reacted overnight at 16° C. using T4 DNA Ligase to carry out ligation reaction. *Escherichia coli* JM109 was transformed with the ligation product. The transformed *Escherichia coli* was cultured and then subjected to miniprep treatment. The obtained DNA was sequenced. The constructed vector was designated as a "phagemid vector pPR3_stuffer_TEV". The operation was performed according to the method described in the paragraph (1-2).

(1-4) Preparation of Randomly Mutated SPINK2 Phagemid Vector

In order to amplify a non-mutated SPINK2 region, a nucleotide sequence (SEQ ID NO: 14) encoding the amino acid sequence of human SPINK2 was used as a template for PCR ((94° C. for 15 seconds, 60° C. for 30 seconds, and 68° C. for 10 seconds)×30 cycles) using the following primers 7 and 8 and KOD-plus-:

Primer 7: 5'-GGTAGCGATATGAGCACCTATGC-3'

Primer 8: 5'-GCACGGACCATTGCGAATA-3'

The amplified fragment was subjected to agarose gel electrophoresis. Then, the desired DNA fragment was excised and purified with Wizard SV Gel and PCR Clean-Up System to prepare DNA. The prepared DNA fragment was designated as Insert A.

Next, each SPINK2 oligonucleotide comprising a random region (region corresponding to the amino acid sequence represented by SEQ ID NO: 1 in the Sequence Listing) was synthesized.

5'-GC AAA TAT CGT ACC CCG AAT TGT UUU UUU UUU UUU UUU VVV UUU TGT VVV UUU UUU WWW XXX CCG GTT GGT AGC GAT ATG-3'

UUU, VVV, WWW, and XXX each represent any base selected from among A, T, G, and C.

UUU includes codons encoding 18 amino acids (Ala, Glu, Gln, Asp, Asn, His, Trp, Arg, Lys, Val, Leu, Ile, Phe, Tyr, Ser, Met, Gly, and Thr) except Cys and Pro.

VVV includes codons encoding 19 amino acids (Ala, Glu, Gln, Asp, Asn, His, Trp, Arg, Lys, Val, Leu, Ile, Phe, Tyr, Ser, Met, Gly, Thr, and Pro) except Cys.

WWW includes codons encoding Tyr, Ser, Phe, Leu, and Thr.

XXX includes codons encoding Asn, Asp, Leu, Lys, Gln, Ala, and Glu.

The Insert A and the SPINK2 oligonucleotide were used as a template for in PCR ((95° C. for 20 seconds, 55° C. for 20 seconds, and 72° C. for 30 seconds)×10 cycles) using the following primers 9 and 10 and PfuUltra II Fusion HS DNA Polymerase (Agilent Technologies, Inc.):

```
Primer 9:
5'-GTTTGGTCTGTTTAGCAAATATCGTACCCCGAATTGT-3'

Primer 10:
5'-GCACGGACCATTGCGAATA-3'
```

The amplified fragment was subjected to agarose gel electrophoresis. Then, the desired DNA fragment was excised and purified with Wizard SV Gel and PCR Clean-Up System to prepare DNA. The prepared DNA fragment was designated as Insert B. The Insert B was further used as a template for PCR ((95° C. for 20 seconds, 55° C. for 20 seconds, and 72° C. for 30 seconds)×10 cycles) using the following primers 11 and 12 and PfuUltra II Fusion HS DNA Polymerase:

```
Primer 11:
5'-AAAGAATTCTGATCCGCAGTTTGGTCTGTTTAGCAAATAATCGT-3'

Primer 12:
5'-AAAGGCGCGCCGCACGGACCATTGCGAATAATTTTAAT-3'
```

The amplified fragment was subjected to agarose gel electrophoresis. Then, the desired DNA fragment was excised and purified with Wizard SV Gel and PCR Clean-Up System to prepare DNA. The prepared DNA fragment was designated as Insert C. The Insert C was treated with restriction enzymes EcoRI (New England Biolabs Japan Inc.) and AscI (New England Biolabs Japan Inc.) at 37° C. for 5 hours or longer, while the phagemid vector pPR3_stuffer_TEV was treated with EcoRI (Takara Bio Inc.) and MluI (Takara Bio Inc.) in the same way as above. The Insert C was purified using Wizard SV Gel and PCR Clean-Up System. The phagemid vector was subjected to agarose gel electrophoresis. Then, the desired DNA fragment was excised and purified with Wizard SV Gel and PCR Clean-Up System (Promega KK.). The purified fragments were reacted overnight at 16° C. using T4 DNA Ligase (New England Biolabs Japan Inc.) to carry out ligation reaction. On the next day, the ligation product was heat-treated at 65° C. for 10 minutes. The DNA was desalted using Amicon-Ultra (30 k; Merck Millipore).

(1-5) Preparation of *Escherichia coli* XL1-Blue Having Randomly Mutated SPINK2 Phagemid Vector Next, competent cells for use in transformation were prepared. XL1-Blue (Stratagene Corp.) cultured overnight on the previous day at 37° C. using a 2-YT medium (Invitrogen Corp.) was inoculated to a 2-YT medium and cultured at 37° C. for a few hours. After ice cooling, pellet was recovered by centrifugation (3,000 g, 10 min., 4° C.) and suspended in sterile water, followed by centrifugation. The pellet was further suspended in 10% glycerol and then centrifuged. The pellet was resuspended in 10% glycerol and then centrifuged. Finally, the pellet was suspended in 10% glycerol to prepare competent cells.

The DNA prepared in the paragraph (1-4) and the competent cells were used in transformation by electroporation (1.97 kV, 186 µF). Then, the cells were shake-cultured at 37° C. for 1 hour using an SOC medium, then plated over a 2-YT plate containing 0.1 mg/ml ampicillin (Wako Pure Chemical Industries, Ltd.) and 2% glucose (Nacalai Tesque, Inc.), and statically cultured at 30° C. On the next day, colonies were recovered using a 2-YT solution containing 1% glucose and 15% glycerol (Wako Pure Chemical Industries, Ltd.) and stored at −80° C. Also, a portion of the culture solution after the electroporation was collected, plated after serial dilution, and statically cultured. On the next day, the number of colonies was measured to estimate the library size. The constructed library was confirmed to have a size of approximately $1.2 \times 10^{10}$ phages.

(1-6) Construction of Randomly Mutated SPINK2 Phage Library

The *Escherichia coli* colonies constructed in the paragraph (1-5) were inoculated to a 2-YT medium containing 0.1 mg/ml ampicillin and 1% glucose to prepare an *Escherichia coli* suspension with $OD_{600\,nm}$=0.3. The bacterial cells were shake-cultured at 37° C. and thereby allowed to grow until $OD_{600\,nm}$=0.5. A sufficient amount of a helper phage VCSM13 (Stratagene Corp.) was added thereto. The cells were left standing at 37° C. for 30 minutes and further shake-cultured at 37° C. for 30 minutes. Then, the cells were left standing on ice for 30 minutes. Pellet was recovered by centrifugation (3,000 g, 20 min., 4° C.), then suspended in a 2-YT medium containing 0.1 mg/ml ampicillin, 30 µg/ml kanamycin (Nacalai Tesque, Inc.), and 0.25 mM IPTG (Wako Pure Chemical Industries, Ltd.), and shake-cultured overnight at 22° C.

On the next day, the culture supernatant was recovered by centrifugation (9,000 g, 20 min., 4° C.). A solution containing 20% polyethylene glycol 6000 (Nacalai Tesque, Inc.) and 2.5 M NaCl (Wako Pure Chemical Industries, Ltd.) was added thereto in ¼ of the amount of the culture supernatant, and the mixture was left standing at 4° C. for 30 minutes to precipitate phage particles (hereinafter, this operation is referred to as "PEG precipitation"). Phages precipitated by two repetitive runs of PEG precipitation and centrifugation (9,000 g, 30 min., 4° C.) were suspended in PBS to prepare a randomly mutated SPINK2 phage library.

*Escherichia coli* XL1-Blue was infected by the prepared phage solution and seeded over a 2-YT plate containing 0.1 mg/ml ampicillin and 1% glucose. The number of formed colonies was measured. The phage library had a titer of $1.8 \times 10^{13}$ phages/ml.

Example 2

Screening for SPINK2 mutant binding to target molecule
(2-1) Liquid-Phase Panning Method Each target protein described in (2-4) was biotinylated using EZ-Link NHS-Chromogenic Biotin Reagent (Thermo) according to the attached instructions.

The biotinylated target protein was mixed with SPINK2 mutant-displaying phages and reacted for 1 to 12 hours. To the reaction product, Dynabeads M-280 Streptavidin (Invitrogen Corp.) (hereinafter, simply referred to as "beads") were added to bind the biotinylated target protein to the beads. The beads were washed a predetermined amount of times with PBS containing 0.05% Tween (hereinafter, referred to as "PBS-T") and then reacted with AcTEV™ Protease (Invitrogen Corp.) for 30 minutes to recover a SPINK2 mutant-displaying phage bound with the biotinylated target protein on the surface of the beads. *Escherichia coli* XL1-Blue was infected by the recovered phage, then seeded over a 2-YT plate containing 0.1 mg/ml ampicillin and 1% glucose, and cultured overnight at 30° C. The randomly mutated SPINK2 phage library was used in the 1st round of liquid-phase panning, and phages prepared from *Escherichia coli* colonies obtained in the preceding round were used in the 2nd or later rounds.

(2-2) Solid-Phase Panning Method

A given amount of each target protein was added to a Nunc Maxisorp flat-bottom 96-well plate (Nunc) and left standing overnight at 4° C. for solid-phase immobilization onto the plate. Also, a given amount of each target protein was added to Pierce NHS-Activated Agarose Dry Resin (Thermo Fisher Scientific K.K.) and immobilized onto agarose according to the attached instruction.

The target protein-immobilized plate or agarose was mixed with SPINK2 mutant-displaying phages and reacted for 1 to 12 hours. To the reaction product, beads were added to bind the biotinylated target protein to the beads. The beads were washed predetermined times with PBS-T and then reacted with AcTEV™ Protease (Invitrogen Corp.) for 30 minutes to recover a SPINK2 mutant-displaying phage bound with the biotinylated target protein on the surface of the beads. *Escherichia coli* XL1-Blue was infected by the recovered phage, then seeded over a 2-YT plate containing 0.1 mg/ml ampicillin and 1% glucose, and cultured overnight at 30° C. The randomly mutated SPINK2 phage library was used in the 1st round of solid-phase panning, and phages prepared from *Escherichia coli* colonies obtained in the preceding round were used in the 2nd or later rounds.

(2-3) Preparation of Phage

The *Escherichia coli* colonies obtained after panning were inoculated to a 2-YT medium containing 0.1 mg/ml ampicillin and 1% glucose to prepare an *Escherichia coli* suspension with $OD_{600\ nm}$=0.3. The bacterial cells were shake-cultured at 37° C. and thereby allowed to grow until $OD_{600\ nm}$=0.5. A sufficient amount of a helper phage VCSM13 (Stratagene Corp.) was added thereto. The cells were left standing at 37° C. for 30 minutes and further shake-cultured at 37° C. for 30 minutes. Then, the cells were left standing on ice for 30 minutes. Pellet was recovered by centrifugation (3,000 g, 20 min., 4° C.), then suspended in a 2-YT medium containing 0.1 mg/ml ampicillin, 30 μg/ml kanamycin (Nacalai Tesque, Inc.), and 0.25 mM IPTG (Wako Pure Chemical Industries, Ltd.), and shake-cultured overnight at 22° C. On the next day, the culture supernatant was recovered by centrifugation. A phage solution was prepared by two repetitive runs of PEG precipitation and centrifugation.

(2-4) Screening for SPINK2 Mutant that Binds to Target Molecule

Three to five rounds of liquid-phase or solid-phase panning were carried out using any one of the following 4 types of target proteins:

Chymotrypsin (Worthington Biochemical Corp.)

Recombinant Human Plasma Kallikrein (R&D Systems, Inc.)

Recombinant Human EGFR/Fc (R&D Systems, Inc.; hereinafter, referred to as "EGFR/Fc")

Recombinant Human ErbB2/Fc (R&D Systems, Inc.; hereinafter, referred to as "HER2/Fc")

(2-5) Evaluation of Binding Activity of SPINK2 Mutant (Polyclone) Against Target Protein SPINK2 mutant-displaying phages were prepared from the *Escherichia coli* colonies after panning according to the method described in the paragraph (2-3).

Each target protein described in the paragraph (2-4) or a negative control IgG-Free Protease-Free Bovine Serum Albumin (Jackson ImmunoResearch Laboratories, Inc.; hereinafter, referred to as "BSA") was added to Nunc Maxisorp flat-bottom 96-well plate (Nunc). The 96-well plate was left standing overnight at 4° C. and thereby coated with the protein. Next, the SPINK2 mutant-displaying phages prepared from the *Escherichia coli* colonies after panning were added thereto as a sample, and the plate was left standing at room temperature for 1 hour. Then, the sample was removed, and the plate was washed with PBS-T. Then, HRP/Anti-M13 Monoclonal Conjugate (GE Healthcare Japan Corp.) was added thereto, and the plate was left standing at room temperature for 1 hour. Then, HRP/Anti-M13 Monoclonal Conjugate was removed, and the plate was washed with PBS-T. Then, the color was developed using POD substrate A.B.T.S. kit (Nacalai Tesque, Inc.). The absorbance was measured at a measurement wavelength of 405 nm. The sample and HRP/Anti-M13 Monoclonal Conjugate were each diluted using PBS-T.

The results are shown in FIGS. 1 to 4. ELISA demonstrated that SPINK2 mutants (polyclones) exhibiting target-specific binding activity were enriched from the randomly mutated SPINK2 library by panning against each target protein.

Example 3

Evaluation of α-Chymotrypsin-Binding Peptide (Single Clone)

(3-1) Construction of pET 32a (Varied)

pIRES Puro3 (Clontech Laboratories, Inc.) was used as a template for PCR ((94° C. for 15 seconds, 60° C. for 30 seconds, and 68° C. for 30 seconds)×30 cycles) using the following primers 13 and 14 and KOD-plus- (Toyobo Co., Ltd.):

5'-AAAGGATCCGCGAATTCATGACCGAGTACAAGCCCAC-3'

5'-AAACTCGAGTTATGCGGCCGCTCAGGCACCGGGCTTGCGG-3'

The amplified fragment was subjected to agarose gel electrophoresis. Then, the desired DNA fragment was excised and purified with Wizard SV Gel and PCR Clean-Up System (Promega KK.) to prepare DNA. The prepared DNA fragment and pET 32a(+) (Novagen, Merck KGaA) were each treated with restriction enzymes BamHI (Takara Bio Inc.) and XhoI (Takara Bio Inc.) at 37° C. for 1 hour or longer. After agarose gel electrophoresis, the desired DNA fragments were excised and purified with Wizard SV Gel and PCR Clean-Up System (Promega KK.). The purified fragments were reacted overnight at 16° C. using T4 DNA Ligase to carry out ligation reaction. *Escherichia coli* JM109 was transformed with the ligation product. The transformed *Escherichia coli* was cultured, followed by miniprep treatment and sequencing to construct "pET 32a (varied)". The operation was performed according to the method described in the paragraph (1-2).

(3-2) Expression of α-Chymotrypsin-Binding Peptide in *Escherichia coli* Origami B (DE3) and Purification Thereof A phagemid vector was recovered from the *Escherichia coli* colonies after panning using QIAGEN Plasmid Midi Kit (Qiagen N.V.) according to the attached instruction. The recovered vector and pET 32a (varied) were each treated with restriction enzymes EcoRI (Takara Bio Inc.) and NotI (Takara Bio Inc.) at 37° C. for 1 hour or longer. After agarose gel electrophoresis, the desired DNA fragments were excised and purified with Wizard SV Gel and PCR Clean-Up System (Promega KK.). The purified fragments were reacted overnight at 16° C. using T4 DNA Ligase (New England Biolabs Japan Inc.) to carry out ligation reaction. *Escherichia coli* JM109 was transformed with the ligation product. The operation was performed according to the method described in the paragraph (1-2). *Escherichia coli* Origami B (DE3) (Novagen, Merck KGaA) was transformed with a plasmid recovered using Miniprep and seeded over a 2-YT plate containing 0.1 mg/ml ampicillin.

Subsequently, the obtained colonies were inoculated to a 2-YT medium containing 0.1 mg/ml ampicillin and cultured overnight at 37° C. Then, a portion of the culture solution was inoculated again to a 2-YT medium containing 0.1 mg/ml ampicillin and cultured until $OD_{600\,nm}$=approximately 1. Then, IPTG (final concentration: 1 mM) was added thereto. Protein expression was induced by overnight culture at 16° C. On the next day, the bacterial cells were collected by centrifugation (3,000 g, 20 min., 4° C.). Then, BugBuster Master Mix (Novagen, Merck KGaA) was added thereto, and the mixture was stirred at room temperature for 20 minutes. TALON Metal Affinity Resin (Takara Bio Inc.) was added to a supernatant recovered by centrifugation (10,000 g, 20 min., 4° C.), and the mixture was stirred at 4° C. for 1 hour or longer to adsorb the His tag-fusion protein of interest onto the resin. The resin was washed several times with a sodium phosphate buffer solution (50 mM sodium phosphate and 300 mM NaCl, pH 7.4). Then, an elution solution (50 mM sodium phosphate, 300 mM NaCl, and 150 mM imidazole, pH 7.4) was added thereto to recover the His tag-fusion protein. In addition, the thioredoxin tag was cleaved using Thrombin cleavage capture kit (Novagen, Merck KGaA). The thioredoxin tag was removed by addition to TALON. Finally, the protein of interest was concentrated and buffer-replaced with PBS using Amicon-Ultra (3 k). The prepared protein of interest (SPINK2 mutant) was subjected to SDS-PAGE under reducing and non-reducing conditions to analyze its molecular state.

The results are shown in FIGS. 5 and 6. All of the clones exhibited a single band under reducing and non-reducing conditions, demonstrating that the molecular state of the protein of interest thus expressed and purified was composed mainly of a monomer.

(3-3) Evaluation of Target-Binding Affinity of α-Chymotrypsin-Binding Peptide Expressed in *Escherichia coli* and Purified Evaluation was conducted by ELISA in order to confirm the target-binding specificity of each SPINK2 mutant (α-chymotrypsin binder) prepared in the paragraph (3-2). The target protein chymotrypsin was added to a Nunc Maxisorp flat-bottom 96-well plate. The 96-well plate was left standing overnight at 4° C. and thereby coated with the protein. Next, the SPINK2 mutant prepared in the paragraph (3-2) was added thereto as a sample, and the plate was left standing at room temperature for 1 hour. Then, the sample was removed and the plate was washed with PBS-T. Then, S-Tag Antibody Affinity Purified HRP conjugated (Bethyl Laboratories, Inc.) was added thereto, and the plate was left standing at room temperature for 1 hour. Then, the detection antibody solution was removed, and the plate was washed with PBS-T. Then, the color was developed using POD substrate A.B.T.S. kit. The absorbance was measured at a measurement wavelength of 405 nm. The sample and S-Tag Antibody Affinity Purified HRP conjugated were each diluted using PBS-T.

The results are shown in FIGS. 7 and 8. All of the SPINK2 mutants prepared using *Escherichia coli* had binding activity against the target. Also, ELISA showed a sigmoid curve. From the lowest value of signal intensity and the maximum response detected in ELISA, a concentration that exhibited 50% of the maximum response, i.e., EC50, was calculated to confirm that EC50 of the binding activity was 18.3 nM in peptide No. 2 (clone 2) and 17.8 nM in peptide No. 6 (clone 6).

(3-4) Evaluation of Target Specificity of 06-Chymotrypsin-Binding Peptide Expressed in *Escherichia coli* and Purified The target protein chymotrypsin or a negative control trypsin (Pierce Biotechnology Inc.) was added to a Nunc Maxisorp flat-bottom 96-well plate. The 96-well plate was left standing overnight at 4° C. and thereby coated with the protein. Next, each SPINK2 mutant prepared in the paragraph (3-2) was added thereto as a sample, and the plate was left standing at room temperature for 1 hour. Then, the sample was removed, and the plate was washed with PBS-T. Then, S-Tag Antibody Affinity Purified HRP conjugated was added thereto, and the plate was left standing at room temperature for 1 hour. Then, the detection antibody solution was removed, and the plate was washed with PBS-T. Then, color was developed using POD substrate A.B.T.S. kit. The absorbance was measured at a measurement wavelength of 405 nm. The sample and S-Tag Antibody Affinity Purified HRP conjugated were each diluted using PBS-T.

The results are shown in FIGS. 9 and 10. Peptide Nos. 2 and 6 (clones 2 and 6) exhibited no reactivity with trypsin and exhibited strong reactivity with the target protein chymotrypsin. These peptides were therefore found to have target-specific binding.

(3-5) Evaluation of Chymotrypsin Inhibitory Activity of α-Chymotrypsin-Binding Peptide Expressed in *Escherichia coli* and Purified The inhibitory activity of each SPINK2 mutant prepared in the paragraph (3-2) against the target protein chymotrypsin was quantified using Pierce Quantitative Protease Assay Kit. The operation was performed according to the attached instruction.

The results are shown in FIG. 11. Peptide Nos. 2 and 6 (clones 2 and 6) both exhibited inhibitory activity and had IC50 of 815 nM and 374 nM, respectively.

(3-6) Sequencing of α-Chymotrypsin-Binding Peptide

Each SPINK2 mutant (α-chymotrypsin-binding peptide) that exhibited binding activity against chymotrypsin in the paragraph (3-3) was sequenced. *Escherichia coli* Origami B (DE3) transformed with a gene of each SPINK2 mutant was cultured overnight at 37° C. using a 2-YT medium containing 0.1 mg/ml ampicillin. On the next day, plasmid DNA was recovered from the culture using QIAprep 96 Turbo Miniprep Kit. The plasmid DNA was used as a template in nucleotide sequence analysis using a primer 15 having the following nucleotide sequence:

```
5'-GTTCTGGTTCTGGCCATATGCACCATC-3'
```

The results of analyzing randomized regions (random regions) are shown in FIG. 12. The randomized regions in all of the SPINK2 mutants were encoded by different nucleotide sequences.

INDUSTRIAL APPLICABILITY

The peptide library of the present invention can be used for searching for peptides that bind to various target molecules and is useful in research on test agents, diagnostic drugs, etc. Also, the peptide that binds to a predetermined target molecule is useful as a test agent, a diagnostic drug, or the like.

Sequence Listing Free Text
SEQ ID NO: 1 in Sequence Listing—Random region of peptide having diversity (FIG. 13)
SEQ ID NO: 2 in Sequence Listing—Random region of chymotrypsin-binding peptide (FIG. 12; peptide No. 1)
SEQ ID NO: 3 in Sequence Listing—Random region of chymotrypsin-binding peptide (FIG. 12; peptide No. 2)
SEQ ID NO: 4 in Sequence Listing—Random region of chymotrypsin-binding peptide (FIG. 12; peptide No. 6)
SEQ ID NO: 5 in Sequence Listing—Random region of chymotrypsin-binding peptide (FIG. 12; peptide No. 7)
SEQ ID NO: 6 in Sequence Listing—Random region of chymotrypsin-binding peptide (FIG. 12; peptide No. 12)
SEQ ID NO: 7 in Sequence Listing—Random region of chymotrypsin-binding peptide (FIG. 12; peptide No. 13)
SEQ ID NO: 8 in Sequence Listing—Random region of chymotrypsin-binding peptide (FIG. 12; peptide No. 14)
SEQ ID NO: 9 in Sequence Listing—Random region of chymotrypsin-binding peptide (FIG. 12; peptide No. 17)
SEQ ID NO: 10 in Sequence Listing—Fragment 1 (FIG. 14)
SEQ ID NO: 11 in Sequence Listing—Fragment 2 (underlined in FIG. 15)
SEQ ID NO: 12 in Sequence Listing—Fragment 3 (FIG. 16)
SEQ ID NO: 13 in Sequence Listing—Fragment 5 (FIG. 17)
SEQ ID NO: 14 in Sequence Listing—Nucleotide sequence encoding amino acid sequence of SPINK2 (FIG. 18)
SEQ ID NO: 15 in Sequence Listing—Amino acid sequence encoded by nucleotide sequence represented by SEQ ID NO: 14 in Sequence Listing
SEQ ID NO: 16 in Sequence Listing—Nucleotide sequence of template DNA for PCR comprising fragments 1 to 5
SEQ ID NO: 17 in Sequence Listing—Primer 1
SEQ ID NO: 18 in Sequence Listing—Primer 2
SEQ ID NO: 19 in Sequence Listing—Primer 1'
SEQ ID NO: 20 in Sequence Listing—Primer 2'
SEQ ID NO: 21 in Sequence Listing—Primer 3
SEQ ID NO: 22 in Sequence Listing—Primer 4
SEQ ID NO: 23 in Sequence Listing—Primer 5
SEQ ID NO: 24 in Sequence Listing—Primer 6
SEQ ID NO: 25 in Sequence Listing—Primer α
SEQ ID NO: 26 in Sequence Listing—Primer β
SEQ ID NO: 27 in Sequence Listing—Primer 7
SEQ ID NO: 28 in Sequence Listing—Primer 8
SEQ ID NO: 29 in Sequence Listing—Primer 9
SEQ ID NO: 30 in Sequence Listing—Primer 10
SEQ ID NO: 31 in Sequence Listing—Primer 11
SEQ ID NO: 32 in Sequence Listing—Primer 12
SEQ ID NO: 33 in Sequence Listing—Primer 13
SEQ ID NO: 34 in Sequence Listing—Primer 14
SEQ ID NO: 34 in Sequence Listing—Primer 15

The invention claimed is:

1. A method for identifying a peptide that binds to a target molecule, wherein the target molecule is a serine protease, and wherein the target molecule is not an endogenous target of SPINK2 selected from trypsin and acrosin, the method comprising the following steps (i) and (ii):
   (i) contacting a plurality of peptides with the target molecule, wherein each of the plurality of peptides has an amino acid sequence with at least 80% sequence identity to SEQ ID NO:15, wherein each peptide comprises an amino acid sequence comprising SEQ ID NO:1 wherein Xaa can be any amino acid except Cys, and wherein each peptide is conjugated at
      (a) its amino terminus to an amino acid sequence encoded by the nucleic acid sequence from the $1^{st}$ base guanine or the $4^{th}$ base cytosine to the $42^{nd}$ base thymine of SEQ ID NO:14, and
      (b) its carboxyl terminus to an amino acid sequence encoded by the nucleic acid sequence from the $94^{th}$ base guanine to the $189^{th}$ base cytosine in SEQ ID NO:14; and
   (ii) recovering the peptide that binds to the target molecule.

2. A method for producing a peptide that binds to a target molecule, wherein the target molecule is a serine protease, and wherein the target molecule is not an endogenous target of SPINK2 selected from trypsin and acrosin, the method comprising the following steps (i) to (iii):
   (i) contacting a plurality of peptides with the target molecule, wherein each of the plurality of peptides has an amino acid sequence with at least 80% sequence identity to SEQ ID NO:15, wherein each peptide comprises an amino acid sequence comprising SEQ ID NO:1 wherein Xaa can be any amino acid except Cys, and wherein each peptide is conjugated at
      (a) its amino terminus to an amino acid sequence encoded by the nucleic acid sequence from the $1^{st}$ base guanine or the $4^{th}$ base cytosine to the $42^{nd}$ base thymine of SEQ ID NO:14, and
      (b) its carboxyl terminus to an amino acid sequence encoded by the nucleic acid sequence from the $94^{th}$ base guanine to the $189^{th}$ base cytosine in SEQ ID NO:14; and
   (ii) recovering a peptide that binds to the target molecule; and
   (iii) preparing, by chemical synthesis, gene recombination, or in vitro translation, a peptide that binds to the target molecule, wherein said peptide corresponds to the peptide recovered in step (ii).

3. A method for determining whether or not a peptide binds to a target molecule, wherein the target molecule is a serine protease, and wherein the target molecule is not an endogenous target of SPINK2 selected from trypsin and acrosin, the method comprising the following steps (i) and (ii):

(i) contacting a plurality of peptides with the target molecule, wherein each of the plurality of peptides has an amino acid sequence with at least 80% sequence identity to SEQ ID NO:15, wherein each peptide comprises an amino acid sequence comprising SEQ ID NO:1 wherein Xaa can be any amino acid except Cys, and wherein each peptide is conjugated at
  (a) its amino terminus to an amino acid sequence encoded by the nucleic acid sequence from the $1^{st}$ base guanine or the $4^{th}$ base cytosine to the $42^{nd}$ base thymine of SEQ ID NO:14, and
  (b) its carboxyl terminus to an amino acid sequence encoded by the nucleic acid sequence from the $94^{th}$ base guanine to the $189^{th}$ base cytosine in SEQ ID NO:14; and (ii) determining that a peptide is positive for binding when the peptide binds to the target molecule.

4. The method of claim 3, further comprising preparing by chemical synthesis, gene recombination, or in vitro translation a peptide that binds to the target molecule, wherein said peptide has the same amino acid sequence as the peptide determined to be positive for binding in step (ii).

5. The method of claim 1, wherein binding of the peptide to the target molecule inhibits proteolytic activity of the target molecule, and wherein the method further comprises step (iii):

(iii) determining that the peptide is positive for inhibition when the peptide inhibits the proteolytic activity of the target molecule.

6. The method of claim 2, wherein binding of the peptide to the target molecule inhibits proteolytic activity of the target molecule, and wherein the method further comprises after step (ii)

determining that the peptide is positive for inhibition when the peptide recovered in step (ii) inhibits the proteolytic activity of the target molecule; and wherein step (iii) comprises preparing, by chemical synthesis, gene recombination, or in vitro translation, a peptide inhibiting the proteolytic activity, wherein said peptide corresponds to the peptide determined to be positive for inhibition.

7. The method of claim 3, wherein the method further comprises:

determining that the peptide is positive for inhibition when the peptide inhibits the proteolytic activity of the target molecule.

8. The method of claim 4, wherein step (ii) further comprises determining that the peptide is positive for inhibition when the peptide inhibits the proteolytic activity of the target molecule; and wherein the method further comprises step (iii) wherein step (iii) comprises preparing, by gene recombination or in vitro translation, a peptide inhibiting the serine protease proteolytic activity, wherein said peptide corresponds to the peptide determined to be positive for inhibition in step (ii).

9. A method for identifying a peptide that binds to a target molecule, wherein the target molecule is a serine protease, and wherein the target molecule is not an endogenous target of SPINK2 selected from trypsin and acrosin, the method comprising the following steps (i) and (ii):

(i) contacting a plurality of peptides with the target molecule, wherein each of the plurality of peptides comprises an amino acid sequence comprising SEQ ID NO:1 wherein Xaa can be any amino acid except Cys, and the plurality of peptides comprises at least one peptide wherein the amino acid sequence corresponding to SEQ ID NO:1 is selected from the group consisting of SEQ ID NOS:2-9; and (ii) recovering the peptide that binds to the target molecule.

10. The method of claim 9, wherein the amino acid sequence comprising SEQ ID NO:1 of each peptide is conjugated at
  (a) its amino terminus directly or via one or two arbitrary amino acids to an amino acid sequence encoded by the nucleic acid sequence from the $1^{st}$ base guanine or the $4^{th}$ base cytosine to the $42^{nd}$ base thymine of SEQ ID NO:14, and/or
  (b) its carboxyl terminus directly or via one or two arbitrary amino acids to an amino acid sequence encoded by the nucleic acid sequence from the $94^{th}$ base guanine to the $189^{th}$ base cytosine in SEQ ID NO:14.

11. The method of claim 9, wherein the each peptide has an amino acid sequence with at least 80% identity to SEQ ID NO:15.

12. The method of claim 9, further comprising preparing, by chemical synthesis, gene recombination, or in vitro translation, a peptide that binds to the target molecule, wherein said peptide has the same amino acid sequence as the peptide recovered in step (ii).

* * * * *

UNITED STATES PATENT AND TRADEMARK OFFICE
CERTIFICATE OF CORRECTION

PATENT NO. : 10,550,154 B2
APPLICATION NO. : 14/420317
DATED : February 4, 2020
INVENTOR(S) : Nishimiya et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 441 days.

Signed and Sealed this
Sixth Day of December, 2022

Katherine Kelly Vidal
*Director of the United States Patent and Trademark Office*